US011562807B2

(12) United States Patent
Maiti et al.

(10) Patent No.: US 11,562,807 B2
(45) Date of Patent: Jan. 24, 2023

(54) SYSTEMS AND METHODS FOR PREDICTING STRUCTURE AND PROPERTIES OF ATOMIC ELEMENTS AND ALLOY MATERIALS

(71) Applicant: Tata Consultancy Services Limited, Mumbai (IN)

(72) Inventors: Soumyadipta Maiti, Pune (IN); Shashank Mishra, Pune (IN); Balarama Sridhar Dwadasi, Pune (IN); Beena Rai, Pune (IN)

(73) Assignee: Tata Consultancy Services Limited, Mumbai (IN)

( * ) Notice: Subject to any disclaimer, the term of this patent is extended or adjusted under 35 U.S.C. 154(b) by 951 days.

(21) Appl. No.: 16/299,699

(22) Filed: Mar. 12, 2019

(65) Prior Publication Data

US 2020/0066376 A1 Feb. 27, 2020

(30) Foreign Application Priority Data

Aug. 23, 2018 (IN) .............................. 201821031567

(51) Int. Cl.
*G16C 20/30* (2019.01)
*G16C 60/00* (2019.01)
*G06F 30/20* (2020.01)

(52) U.S. Cl.
CPC ............. *G16C 20/30* (2019.02); *G06F 30/20* (2020.01); *G16C 60/00* (2019.02)

(58) Field of Classification Search
None
See application file for complete search history.

(56) References Cited

U.S. PATENT DOCUMENTS

| | | | |
|---|---|---|---|
| 2003/0216867 A1 | 11/2003 | Campbell et al. | |
| 2012/0232685 A1* | 9/2012 | Wang | G06F 30/23 700/98 |
| 2014/0039851 A1* | 2/2014 | Heinz | G16C 10/00 703/2 |

FOREIGN PATENT DOCUMENTS

CN 101957285 1/2011

OTHER PUBLICATIONS

Daw, M.S.; Foiles, S. M.; Baskes, M. I. The Embedded-Atom Method: A Review of Theory and Applications. Materials Science Reports 1993, 9 (7-8), 251-310.*

(Continued)

*Primary Examiner* — Soren Harward
(74) *Attorney, Agent, or Firm* — Finnegan, Henderson, Farabow, Garrett & Dunner, LLP

(57) ABSTRACT

Metallic alloy development has been traditionally based on experimental or theoretical equilibrium phase diagrams and the like. The synthesis, processing and mechanical testing of small and large real samples are a challenging task requiring huge amount of effort in terms of time, money, resource, tedious testing and processing equipment and man-hour for which conventional Calphad calculations etc. alone do not help much in their local structure and related property prediction. Embodiments of the present disclosure provide simulation systems and methods for structure evolution and property prediction Molecular Dynamics (MD) combined with accelerated Monte Carlo techniques, wherein information on atomic elements and composition specific to alloy material is obtained to generate a MD potential file that is further used to generate a 3D structure file by executing a structure equilibration technique. An optimized evolved 3D (Continued)

structure file is then generated that has atomic positions output and/or thermodynamic output for predicting properties.

9 Claims, 14 Drawing Sheets

(56) References Cited

OTHER PUBLICATIONS

Sandia Corporation. LAMMPS Users Manual. 2003.*
Bringa, E. M.; Wirth, B. D.; Caturla, M. J.; Stölken, J.; Kalantar, D. Metals Far from Equilibrium: From Shocks to Radiation Damage. Nuclear Instruments and Methods in Physics Research Section B: Beam Interactions with Materials and Atoms 2003, 202, 56-63.*
Mulliah, D. Molecular Dynamics Simulations of Nanofriction and Wear. Doctoral Thesis, Loughborough University, Loughborough, England, 2004.*
Widom, M. et al. (Jan. 2014). "Hybrid Monte Carlo/molecular dynamics simulation of a refractory metal high entropy alloy," *Metallurgical and Materials Transactions A*, vol. 45, issue 1; pp. 196-200.
Smith, H. et al. (Apr. 2017). "A Case Study in Manual and Automated Monte Carlo Variance Reduction with a Deep Penetration Reactor Shielding Problem," *Nuclear Science and Engineering*, vol. 149, No. 1; pp. 23-37.

* cited by examiner

SYSTEMS AND METHODS FOR PREDICTING STRUCTURE AND PROPERTIES OF ATOMIC ELEMENTS AND ALLOY MATERIALS

PRIORITY CLAIM

This U.S. patent application claims priority under 35 U.S.C. § 119 to: India Application No. 201821031567, filed on Aug. 23, 2018. The entire contents of the aforementioned application are incorporated herein by reference.

TECHNICAL FIELD

The disclosure herein generally relates to multi-scale modeling of atomic elements and alloy materials, and, more particularly, to systems and methods for predicting structure and properties of atomic elements and alloy materials thereof.

BACKGROUND

Traditionally metallic alloy development has been based on past experiences and on some experimental or theoretical equilibrium phase diagrams etc. The synthesis, processing and mechanical testing of small and large real samples are a challenging task requiring huge amount of effort in terms of time, money, resource, tedious testing and processing equipment and man-hours. Moreover most of the engineering metallic materials have non-equilibrium or metastable structures for which conventional Calphad calculations etc. alone do not help much in their local structure and related property prediction. Also the long-term performance prediction remains a challenge for metals and alloys as it is largely dependent on experiences and long experiments, raising the barrier for time to market products.

SUMMARY

Embodiments of the present disclosure present technological improvements as solutions to one or more of the above-mentioned technical problems recognized by the inventors in conventional systems. For example, in one aspect, there is provided a processor implemented method for predicting structure and properties of atomic elements and alloy materials thereof. The method comprises receiving, via one or more hardware processors, information pertaining to at least one of a plurality of atomic elements, and associated composition thereof specific to an alloy material, wherein the plurality of atomic elements comprise of one or more atomic metallic elements; generating, via the one or more hardware processors, a Molecular Dynamics Potential (MDP) file comprising sequential data of similar and dissimilar atomic interactions of the plurality of atomic elements based on the information; generating, via a structure equilibration executed by the one or more hardware processors, a Three-Dimensional (3D) structure file for the associated composition of each of the plurality of atomic elements specific to the alloy material by using the MDP file, wherein Three-Dimensional (3D) structure file comprises 3D coordinates for each of the plurality of atomic elements and associated type thereof; and generating, via one or more Monte Carlo applications executed by the one or more hardware processors, an optimized evolved 3D structure file comprising at least one of an atomic positions output and a thermodynamic output, by using the 3D structure file and one or more heat treatment schemes, wherein one or more properties pertaining to the plurality of atomic elements and associated composition thereof specific to the alloy material are predicted by using at least one of the atomic positions output and the thermodynamic output.

In an embodiment, the method may further comprise introducing one or more line defects and dislocations in the optimized evolved 3D structure file for predicting structure evolution and mechanical properties of the alloy material.

In an embodiment, the Molecular Dynamics Potential (MDP) file is generated based on the information and by calculating an embedded function for each of the plurality of the atomic elements and one or more parameters pertaining to pairwise interaction of the plurality of the atomic elements.

In an embodiment, the atomic positions output comprises of at least one of local composition of the plurality of atomic elements, Short-range-order/short-range clustering (SRO/SRC) of the plurality of atomic elements, lattice distortion of local atomic structure of the plurality of atomic elements, local strains of the local atomic structure of the plurality of atomic elements, one or more defects, nano-clusters of the plurality of atomic elements, one or more morphological changes comprising distribution of the plurality of atomic elements, one or more Phase Field (PF) parameters, one or more interfaces of phases or clusters in the plurality of atomic elements, an evolution sequence of the alloy material, real time-scale prediction of structure evolution of the alloy material.

In an embodiment, the thermodynamic output comprises at least one of lattice potential energy of the plurality of atomic elements, a change in enthalpy of the plurality of atomic elements, a change in Gibbs free energy of the plurality of atomic elements and a change in entropy of the plurality of atomic elements, Stacking Fault Energy (SFE) of the plurality of atomic elements, local thermodynamic changes of the plurality of atomic elements, and phonons of the plurality of atomic elements.

In another aspect, there is provided a system for predicting structure and properties of atomic elements and alloy materials thereof. The system comprises: a memory storing instructions; one or more communication interfaces; and one or more hardware processors coupled to the memory via the one or more communication interfaces, wherein the one or more hardware processors are configured by the instructions to: receive information pertaining to at least one of a plurality of atomic elements, and associated composition thereof specific to an alloy material, wherein the plurality of atomic elements comprise of one or more atomic metallic elements; generate a Molecular Dynamics Potential (MDP) file comprising sequential data of similar and dissimilar atomic interactions of the plurality of atomic elements based on the information; generate, via a structure equilibration executed by the one or more hardware processors, a Three-Dimensional (3D) structure file for the associated composition of each of the plurality of atomic elements specific to the alloy material by using the MDP file, wherein Three-Dimensional (3D) structure file comprises 3D coordinates for each of the plurality of atomic elements and associated type thereof; and generate, via one or more Monte Carlo applications executed by the one or more hardware processors, an optimized evolved 3D structure file comprising at least one of an atomic positions output and a thermodynamic output, by using the 3D structure file and one or more heat treatment schemes, wherein one or more properties pertaining to the plurality of atomic elements and associated composition thereof specific to the alloy material are predicted by using at least one of the atomic positions output and the thermodynamic output.

In an embodiment, the one or more hardware processors are further configured by the instructions to introduce one or more line defects and dislocations in the optimized evolved 3D structure file for predicting structure evolution and mechanical properties of the alloy material.

In an embodiment, the Molecular Dynamics Potential (MDP) file is generated based on the information and by calculating an embedded function for each of the plurality of the atomic elements and one or more parameters pertaining to pairwise interaction of the plurality of the atomic elements.

In an embodiment, the atomic positions output comprises of at least one of local composition of the plurality of atomic elements, Short-range-order/short-range clustering (SRO/SRC) of the plurality of atomic elements, lattice distortion of local atomic structure of the plurality of atomic elements, local strains of the local atomic structure of the plurality of atomic elements, one or more defects, nano-clusters of the plurality of atomic elements, one or more morphological changes comprising distribution of the plurality of atomic elements, one or more Phase Field (PF) parameters, one or more interfaces of phases or clusters in the plurality of atomic elements, an evolution sequence of the alloy material, real time-scale prediction of structure evolution of the alloy material.

In an embodiment, the thermodynamic output comprises at least one of lattice potential energy of the plurality of atomic elements, a change in enthalpy of the plurality of atomic elements, a change in Gibbs free energy of the plurality of atomic elements and a change in entropy of the plurality of atomic elements, Stacking Fault Energy (SFE) of the plurality of atomic elements, local thermodynamic changes of the plurality of atomic elements, and phonons of the plurality of atomic elements.

In yet another aspect, there are provided one or more non-transitory machine readable information storage mediums comprising one or more instructions which when executed by one or more hardware processors causes predicting structure and properties of atomic elements and alloy materials thereof by receiving, via the one or more hardware processors, information pertaining to at least one of a plurality of atomic elements, and associated composition thereof specific to an alloy material, wherein the plurality of atomic elements comprise of one or more atomic metallic elements; generating, via the one or more hardware processors, a Molecular Dynamics Potential (MDP) file comprising sequential data of similar and dissimilar atomic interactions of the plurality of atomic elements based on the information; generating, via a structure equilibration executed by the one or more hardware processors, a Three-Dimensional (3D) structure file for the associated composition of each of the plurality of atomic elements specific to the alloy material by using the MDP file, wherein Three-Dimensional (3D) structure file comprises 3D coordinates for each of the plurality of atomic elements and associated type thereof; and generating, via one or more Monte Carlo applications executed by the one or more hardware processors, an optimized evolved 3D structure file comprising at least one of an atomic positions output and a thermodynamic output, by using the 3D structure file and one or more heat treatment schemes, wherein one or more properties pertaining to the plurality of atomic elements and associated composition thereof specific to the alloy material are predicted by using at least one of the atomic positions output and the thermodynamic output.

In an embodiment, the method may further comprise introducing one or more line defects and dislocations in the optimized evolved 3D structure file for predicting structure evolution and mechanical properties of the alloy material.

In an embodiment, the Molecular Dynamics Potential (MDP) file is generated based on the information and by calculating an embedded function for each of the plurality of the atomic elements and one or more parameters pertaining to pairwise interaction of the plurality of the atomic elements.

In an embodiment, the atomic positions output comprises of at least one of local composition of the plurality of atomic elements, Short-range-order/short-range clustering (SRO/SRC) of the plurality of atomic elements, lattice distortion of local atomic structure of the plurality of atomic elements, local strains of the local atomic structure of the plurality of atomic elements, one or more defects, nano-clusters of the plurality of atomic elements, one or more morphological changes comprising distribution of the plurality of atomic elements, one or more Phase Field (PF) parameters, one or more interfaces of phases or clusters in the plurality of atomic elements, an evolution sequence of the alloy material, real time-scale prediction of structure evolution of the alloy material.

In an embodiment, the thermodynamic output comprises at least one of lattice potential energy of the plurality of atomic elements, a change in enthalpy of the plurality of atomic elements, a change in Gibbs free energy of the plurality of atomic elements and a change in entropy of the plurality of atomic elements, Stacking Fault Energy (SFE) of the plurality of atomic elements, local thermodynamic changes of the plurality of atomic elements, and phonons of the plurality of atomic elements.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this disclosure, illustrate exemplary embodiments and, together with the description, serve to explain the disclosed principles.

DETAILED DESCRIPTION

Figure 1:
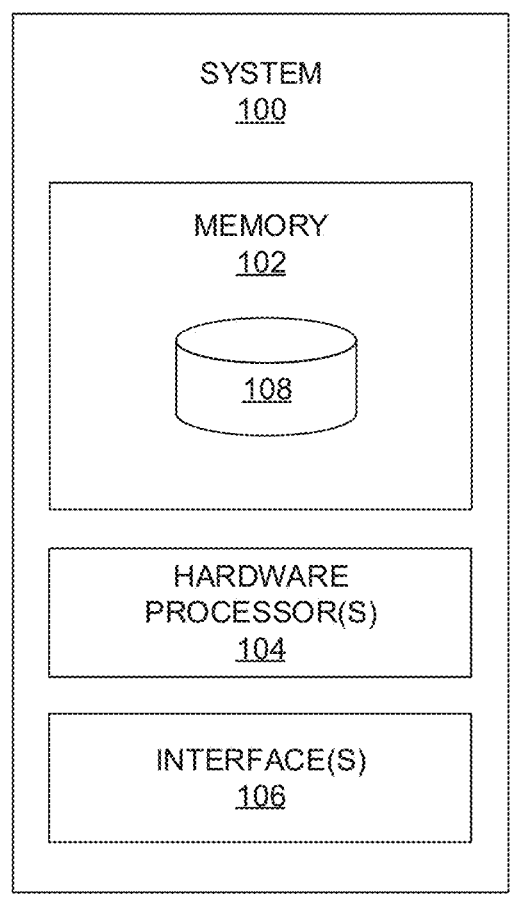
FIG. 1 illustrates an exemplary block diagram of a system for predicting structure and properties of atomic elements and alloy materials thereof in accordance with an embodiment of the present disclosure.

Exemplary embodiments are described with reference to the accompanying drawings. In the figures, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the spirit and scope of the disclosed embodiments. It is intended that the following detailed description be considered as exemplary only, with the true scope and spirit being indicated by the following claims.

Metallic alloys comprise of wide varieties of structures such as solid solutions, intermetallic and Bulk Metallic Glasses (BMG). Alloys are generally much more superior than constituting major elements in terms of strength, toughness, corrosion resistance, thermal properties etc. The common alloys in practical uses are Fe, Ni, Al, Ti-based alloys. Due to ongoing scientific research and development activities, new Mg, Cu, Co, refractory-based and complex concentrated alloys (like high-entropy alloys) etc. are getting importance as functional and futuristic alloys. Usually in conventional solid solution alloys, the matrix comprises of one principal element based single/multi-phase body/face-centered cubic (BCC/FCC) substitutional/interstitial structure. But in complex concentrated alloys there may be multiple principal alloying elements present.

The synthesis, processing and mechanical testing of small and large real samples are a challenging task requiring huge amount of effort in terms of time, money, resource, tedious testing and processing equipment and man-hours. As discussed above, most of the engineering metallic materials have non-equilibrium or metastable structures for which conventional Calphad calculations etc. alone do not help much in their local structure and related property prediction. In engineering applications, temperature and time dependent local structural evolution involving short-range ordering/clustering (SRO/SRC), nano-precipitate phase etc. significantly affect material performance properties. Long-term performance prediction thus remains a challenge for metals and alloys as it is largely dependent on experiences and long experiments, raising the barrier for product launching. Although there are a lot of alloys commercially available for example, over 1000 steel grades, there is a need for new product and process dependent property improvements. New high performance product development as a whole is largely based on a lot of trial-error methods and people often do not have a directed guidance for the product development. Alloy development and product launching in the conventional way at its present condition can take around staggering 10-20 years approximately.

Referring now to the drawings, and more particularly to FIGS. 1 through 14B, where similar reference characters denote corresponding features consistently throughout the figures, there are shown preferred embodiments and these embodiments are described in the context of the following exemplary system and/or method.

FIG. 1 illustrates an exemplary block diagram of a system for predicting structure and properties of atomic elements and alloy materials thereof in accordance with an embodiment of the present disclosure. In an embodiment, the system 100 includes one or more processors 104, communication interface device(s) or input/output (I/O) interface(s) 106, and one or more data storage devices or memory 102 operatively coupled to the one or more processors 104. The one or more processors 104 may be one or more software processing modules and/or hardware processors. In an embodiment, the hardware processors can be implemented as one or more microprocessors, microcomputers, microcontrollers, digital signal processors, central processing units, state machines, logic circuitries, and/or any devices that manipulate signals based on operational instructions. Among other capabilities, the processor(s) is configured to fetch and execute computer-readable instructions stored in the memory. In an embodiment, the device 100 can be implemented in a variety of computing systems, such as laptop computers, notebooks, hand-held devices, workstations, mainframe computers, servers, a network cloud and the like.

The I/O interface device(s) 106 can include a variety of software and hardware interfaces, for example, a web interface, a graphical user interface, and the like and can facilitate multiple communications within a wide variety of networks N/W and protocol types, including wired networks, for example, LAN, cable, etc., and wireless networks, such as WLAN, cellular, or satellite. In an embodiment, the I/O interface device(s) can include one or more ports for connecting a number of devices to one another or to another server.

The memory 102 may include any computer-readable medium known in the art including, for example, volatile memory, such as static random access memory (SRAM) and dynamic random access memory (DRAM), and/or non-volatile memory, such as read only memory (ROM), erasable programmable ROM, flash memories, hard disks, optical disks, and magnetic tapes. In an embodiment a database 108 can be stored in the memory 102, wherein the database 108 may comprise, but are not limited to information pertaining to atomic elements and their composition that are specific to alloy material(s), output(s) generated by one or more simulation technique(s), one or more modeling technique(s), etc. In an embodiment, the memory 102 may store the one or more modeling technique(s), the one or more simulation technique(s), which are executed by the one or more hardware processors 104 to perform the methodology described herein.

Figure 2:
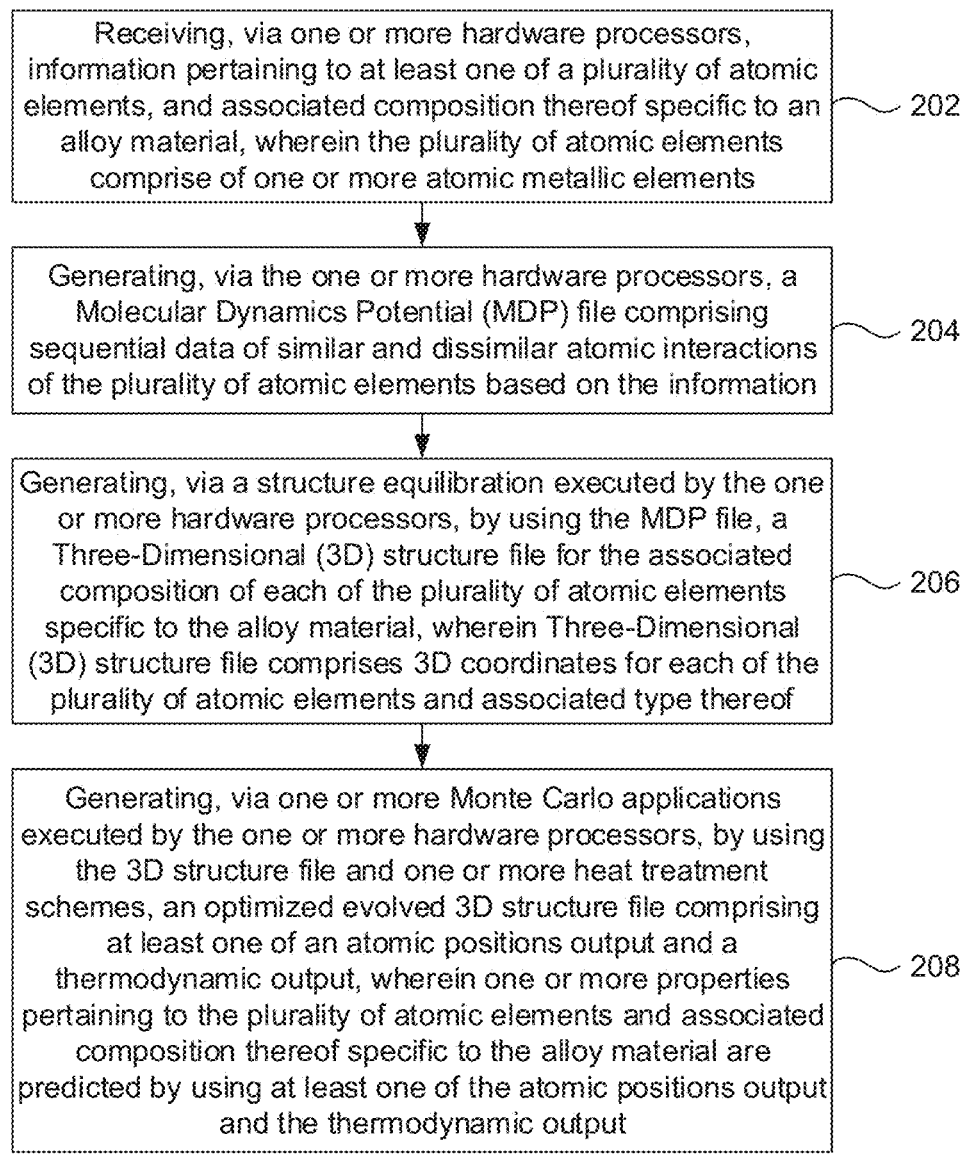
FIG. 2 illustrates an exemplary flow diagram of a method for predicting structure and properties of atomic elements and alloy materials thereof using the system 100 of FIG. 1 in accordance with an embodiment of the present disclosure.

FIG. 2, with reference to FIG. 1, illustrates an exemplary flow diagram of a method for predicting structure and properties of atomic elements and alloy materials thereof using the system 100 of FIG. 1 in accordance with an embodiment of the present disclosure. In an embodiment, the system(s) 100 comprises one or more data storage devices or the memory 102 operatively coupled to the one or more hardware processors 104 and is configured to store instructions for execution of steps of the method by the one or more processors 104. The steps of the method of the present disclosure will now be explained with reference to the components of the system 100 as depicted in FIG. 1, and the flow diagram. In an embodiment of the present disclosure, at step 202, the one or more hardware processors 104 receive information pertaining to a plurality of atomic elements (also referred as 'atomic elements' and may be interchangeably used hereinafter) and their corresponding compositions. The atomic elements and the associated composition are specific to an alloy material, wherein the plurality of atomic elements comprise of one or more atomic metallic elements and optionally one or more non-metallic elements/one or more atomic non-metallic elements (e.g., carbon).

In an embodiment of the present disclosure, at step 204, the one or more hardware processors 104 generate a Molecular Dynamics Potential (MDP) file comprising sequential data of similar and dissimilar atomic interactions of the plurality of atomic elements based on the information. In an embodiment, metallic alloy material as created initially may be primarily studied by MD simulations for its structural property evaluations. In the present disclosure, EAM type or hybrid EAM+LJ (Embedded-atom method+Lennard-Jones) or Tershoff type potentials etc., is used for generated the MDP file. Based on the elements present in the alloy, MD potential files will be generated and used accordingly. Externally provided EAM or modified EAM potentials can also be used in combination with the generated potentials, in one example embodiment. In an embodiment of the present disclosure, the Molecular Dynamics Potential (MDP) file is generated based on the information and by calculating an embedded function for each of the plurality of the atomic elements and one or more parameters (e.g., force distance curves—derived from physical constants, or handbook) pertaining to pairwise interaction (e.g., 2 body or multi-body interaction such as atom number 10 and atom number 15) of the plurality of the atomic elements.

The embedded function and pairwise interaction are obtained by receiving inputs from physical constants, scaling analysis, and from first principle and literature, etc. Input parameters from elemental physical constants may comprise but are not limited to cohesive energy, vacancy formation energy, lattice parameters, atomic radius, second order elastic stiffness constants, anisotropic ratio etc. which get utilized for the construction of the Embedding function and pairwise atomic interactions.

Likewise, inputs from scaling analysis include but are not limited to, electron density around atoms from different references, shapes and trends of embedding function and pairwise interactions of different materials from literature may be compared and scaled. This analysis is then used to create Embedding function and Pairwise interactions for new systems under study.

Similarly, inputs from first principle and literature, Potfit program is used, and materials handbook and other academic publications for Embedded-Atom Method (EAM), MEAM (Modified Embedded Atom Method) or LJ type interactions etc. can be analyzed for a proper choice for the development of unknown pairwise-interactions, Ab-initio based MD of alloy system and multiple configuration study.

Referring to step 206, in an embodiment of the present disclosure, the one or more hardware processors 104 generate, via a structure equilibration (also referred hereinafter as 'structure equilibration technique'), a Three-Dimensional (3D) structure file for the associated composition of each of the plurality of atomic elements specific to the alloy material by using the MDP file. In an embodiment, the Three-Dimensional (3D) structure file comprises 3D coordinates for each of the plurality of atomic elements and associated type thereof. In an embodiment, the 3D structure file generation is an initial stage on the structure evolution scheme, where the real/hypothetical local structure may be first stabilized/equilibrated by NPT/NVT/NVE based MD or MS method, wherein NPT refers to Constant pressure and temperature, NVT refers to Constant volume and temperature, and NVE refers to Constant volume and energy. The initial input for the structure should contain the constituting elements of the metallic material and their stoichiometric ratios. The average structural framework type for example, solid solutions (BBC, FCC or Hexagonal Closed Packed (HCP)), Intermetallics and Bulk Metallic Glass (BMGs) are generated in the structure equilibration process. The structure may or may not contain the initial structural defects and the structural equilibration is done based on the created MD potential file.

In an embodiment of the present disclosure, at step 208, the one or more hardware processors 104 generate, via one or more Monte Carlo applications executed by the one or more hardware processors, an optimized evolved 3D structure file by using the 3D structure file and one or more heat treatment schemes. The optimized evolved 3D structure file comprises at least one of an atomic positions output and a thermodynamic output.

Using the one or more heat treatment schemes, the temperature schedules of a system under investigation may be programmed or tabulated for its structural evolution. The heat treatment schedule is fed as an input to the one or more Monte Carlo (MC) applications. The MC application(s) (e.g., also referred as MD combined with Monte Carlo (a kind of statistical sampling process) techniques) is implemented and executed by the system 100 for the evolution of local structure. In an embodiment, the MC application(s) can either be executed automatically or by way of one or more inputs from user(s) (e.g., manual mode). In an embodiment, the initial structures may or may not contain structural defects for example, dislocations, stacking faults, etc. In the absence of line-defects, dislocations and the like, the hardware processors 104 may further be configured to introduce one or more line defects and dislocations in the optimized evolved 3D structure file for predicting structure evolution and mechanical properties of the alloy material in on example embodiment. The evolved atomic structures can be saved at some fixed MC intervals or at user(s) discretion.

During an automatic mode operation of the MC application(s), the system 100 takes temperature inputs from the heat-treatment schemes and equilibrates the initial local structure. NPT simulation by system specific MD potentials would indicate the average Lattice Parameter (LP) of the initial structure and this LP may be transferred to a lattice energy simulation technique. For high temperature heat treatment schedules, the LP may be numerically extrapolated from lower temperature NPT simulations of stable lattice structures.

When the lattice energy simulation technique is executed by the system 100, at first the lattice energy may be minimized by Conjugate Gradient (CG) or Hessian-free truncated Newton (HFTN) etc. methods while keeping the average LP constant. During structure evolution, average LP can be changed when the simulation system has experienced 1 attempted atomic swaps/atom. Atoms are swapped with respect to their previous positions towards new positions. The atoms can be chosen randomly from any lattice site, neighboring sites, other sub-lattice or interstitial sites as well. Swaps can be between either two atoms, atom and vacancy or between a cluster of atoms. Other than the atomic swap, swaps between different local structural configurations may be performed which would continuously evolve during the running of this MC application(s) at different temperatures. The swapping between two atomic configurations may be accepted by a probability, which is by default given by established Metropolis-type MC as the default automatic method. After one accepted atomic swap, the structure is transferred again to Lattice energy minimization technique until the structure evolves.

During a manual (or user assisted) mode operation of the MC application(s) execution, the system 100 enables to perform the following:
1. Lattice energy minimization with CG/HFTN methods with fixed LP
2. Hybrid MC techniques like user defined NPT/NVT equilibration steps between atomic swaps
3. More than 2 atom swaps, replica exchange, cluster swap method etc.
4. Relaxation of LP by NPT simulation intermittently between one or more atomic swaps During the user assisted mode operation of the MC application(s) atoms are swapped with respect to their previous positions towards new positions. One or more atoms can be chosen randomly from any lattice site, neighboring sites, other sub-lattice or interstitial sites as well. Swaps can be between either two atoms, atom and vacancy or between a cluster of atoms. Other than the atomic swap, swaps between different local structural configurations can also be performed which would continuously evolve during the running of the MC application(s) at different temperatures. The swapping between two atomic configurations may be accepted by a probability, which is calculated from Metropolis/Glauber/Swendsen-Wang etc., type MC criteria.

Upon executing the above techniques, one or more properties pertaining to the plurality of atomic elements and associated composition thereof specific to the alloy material are predicted by using at least one of the atomic positions output and the thermodynamic output.

The atomic positions output is generated by extracting the atomic coordinates and the atom types of the MC output structure. By post processing the coordinates of the evolved local structure, any traces of SRO/SRC can be identified, local strains and atomic relaxation displacements can be quantified, and defect cluster evolution, morphological changes in local chemical compositions, structure evolution sequence etc. can be obtained. Also directional local composition scan, quantification of the morphologies of SRO/SRC/nano-precipitates can be performed.

In other words, the atomic positions output comprises of at least one of local composition of the plurality of atomic elements, Short-range-order/short-range clustering (SRO/SRC) of the plurality of atomic elements, lattice distortion of local atomic structure of the plurality of atomic elements, local strains of the local atomic structure of the plurality of atomic elements, one or more defects, nano-clusters of the plurality of atomic elements, one or more morphological changes comprising distribution of the plurality of atomic elements, one or more Phase Field (PF) parameters (e.g., micro and milli meter scaling parameters (or multi-scale modeling technique(s))), one or more interfaces of phases or clusters in the plurality of atomic elements, an evolution sequence of the alloy material, real time-scale prediction of structure evolution of the alloy material.

By analyzing the MC evolved structures, thermodynamic properties can be obtained such as Lattice potential energy, $\Delta H$ (Change in enthalpy), $\Delta G$ (change in Gibbs free energy), $\Delta S$ (change in entropy), SFE (Stacking Fault Energy), local thermodynamic changes with MC sequence, internal energy and phonons. Also the interfacial energy of the SRO/SRC/nano-precipitates with respect to the adjacent matrix can be obtained quantitatively/semi-quantitatively.

In other words, the thermodynamic output comprises at least one of lattice potential energy of the plurality of atomic elements, a change in enthalpy of the plurality of atomic elements, a change in Gibbs free energy of the plurality of atomic elements and a change in entropy of the plurality of atomic elements, Stacking Fault Energy (SFE) of the plurality of atomic elements, local thermodynamic changes of the plurality of atomic elements, and phonons of the plurality of atomic elements.

The system 100 further enables properties prediction without Molecular Dynamics wherein certain mechanical properties can be obtained without performing any further MD simulations. This can include extra strengthening due to the formation of SRO/SRC/nano-precipitates, their number densities, relative morphology and dispersions in the alloy matrix. Also the stacking fault energy, local lattice distortions and variation of lattice potential energy etc. can provide qualitative/semi quantitative information about the mechanical properties of alloys.

In an embodiment, MC evolved structures may contain SRO/SRC or nano-precipitates which add extra strength to the alloy. The change in local potential energy of the evolved structure is compared with respect to the initial structure before MC. This change in internal potential energy may be related to the strengthening effect. Also, the average size and spacing between the nano-precipitates/SROs obtained from the "Atomic positions output" can be related to the strengthening effects due to dislocation activities.

Systems which show growth or evolution of SRO/SRC/nano-precipitates by MC simulations, Phase-field and microstructure modeling parameters are of importance for multi-scale microstructure modeling. The "interfacial energy" of the SRO/SRC/nano-precipitates and their morphological "strength of anisotropy" may be utilized in Phase-field modeling. Also the growth and local compositional aspects of the SRO/SRC/nano-precipitates can be modelled for larger micron-scale microstructure by multi-scale modelling methods like cellular automata etc.

The system 100 enables properties prediction with Molecular Dynamics by simulating the obtained atomistic structures by different types of MD methodologies applicable for different types of property predictions. These predicted properties could be of types, for example, but are not limited to: Strengthening effects, dislocation mobility, fracture, plasticity, Cohesive zone modeling (CZM), nano-indentation, wear and radiation/defect damage related properties etc.

In other words, properties prediction with Molecular Dynamics may be performed by (i) addition of line defects and dislocations, (ii) executing Deformation stress application(s), (iii) using Strengthening outputs, (iv) creation of Fracture surface/interface, (v) executing Fracture/debonding stress application (s), (vi) using Fracture related outputs, (vii) executing Indentation simulation, (viii) executing Scratch simulation, (ix) using wear properties, (x) Particle bombarding, (xi) Radiation damage, and the like.

Addition of line defects and dislocations: Line defects such as edge, screw or mixed dislocations are created and other structural defects for example, vacancy or interstitial loops are introduced.

Deformation stress application execution: The mechanical properties of the metal/alloy may be obtained by moving the dislocations created as discussed above. The stress application can be executed in a shear mode on the top surface atoms keeping the bottom surface atoms fixed to subject the simulated system for dislocation movement and the required shear stress level can be obtained.

Strengthening outputs: Strengthening refers to means ratio of the deformation stress of the investigated material with respect to that predicted by pure elements from rule of mixture. The measures of strengthening can either come from simulations involving dislocation movement or nano-indentation etc. Also the velocities of dislocation movement under different applied stress levels gives dislocation mobility parameters, which can be useful to multi-scale modeling involving dislocation dynamics and crystal plasticity. The results obtained might be quantitative or semi-quantitative in nature, in one example embodiment.

Fracture surface/interface creation: A notch in the system under investigation may be created for fracture and create 2-material interface for fracture/debonding investigations. The notch can be created by deleting some atoms at particular crystallographic input directions.

Fracture/debonding stress application execution: For fracture simulations, stress is applied to the atomistic structure in different user input loading directions and modes. The tensile or shear stress may be applied to some particular surface atoms while keeping the opposite surface atoms fixed.

Fracture related outputs: By applying the stress at the notch and interfaces, the stress versus deformation/debonding curves can be obtained for various crystallographic orientations and stress loading modes. This gives the quantitative/semi-quantitative ideas on fracture energy and CZM energy for debonding, indication of ductility, etc. The atomic structural changes during the fracture stress applications is captured by saving the structural coordinates. This indicates the local stress levels in fracture/debonding and/or any local structural phase transformations under the stresses. Deforming/fracturing system under consideration can also be done by nano-indentation simulations and quantitative/semi-quantitative idea about plasticity and fracture can also be obtained from indentations.

Indentation simulation: In Non-scale indentation simulations, a mutually rigid group of atoms/metal-atom indenter can act as one block and the alloy material can be treated as a second block. The first block of atoms can be pressed/indented on the second block either by imposed displacement/external force. The consequential atomic movements on the second block of atoms are stored for their 3-d coordinate and internal stresses. The state of plastic deformations obtained from the local co-ordinates and internal stresses are transferred to the outputs related to strengthening, plasticity and fracture toughness.

Scratch simulation: Nano-scale scratch simulations may be performed by dividing the atoms into two groups, namely the scratch-indenter and the investigated alloy. Similar to the "indentation simulation", a first block of atoms can be pressed/indented on a second block either by imposed displacement/external force. Then the first indenter block is given a lateral displacement towards the length of the second block of atoms. During the indenter displacement, the atomic coordinates are saved to account for plastic deformation and material pull-up by the indenter.

Wear properties: Systems of atomic structural coordinates generated by the "Scratch simulation" technique. By analyzing the internal/surface plastic deformation and material pull-up by the indenter, a quantitative/semi-quantitative measure of the wear resistance property is obtained.

Particle bombarding: This simulation technique enables to simulate the phenomena of shooting atoms/particles of different mass and energy towards a block/surface of the atomic structure of the metal/alloy. Here user(s) can define the particle bombarding parameters for example, the mass of particle, angle, velocity, etc. The atomic-coordinates of a system under consideration are saved for further analysis of radiation damage. The output structure can again be coupled to "Monte Carlo application(s)" to accelerate the local structural evolutions.

Radiation damage: Structural-coordinate data from the particle bombarding technique are taken wherein the atomic co-ordinates are analyzed and pointed out for the types of local structural defects/radiation damage produced by "Particle bombarding". Quantification of radiation damage is based on the number of vacancy/interstitial sites/vacancy-loops/local stacking faults created in the alloy atomic structure.

Experimental Validation of the Above Simulation Technique(s):

In the present disclosure, developed structure evolution and property prediction has been tested for a well characterized equiatomic $Ta_{0.25}Nb_{0.25}Hf_{0.25}Zr_{0.25}$ high-entropy alloy (HEA) system (or structure). This alloy contains high melting temperature refractory elements and this type of HEAs are potential candidate for high temperature and high strength materials for functional and aerospace applications, etc. The average structure type, lattice parameters and local real structure, local chemical compositions with respect to high-temperature annealing has been well characterized. The effect of long term annealing heat treatment on the mechanical properties such as hardness, strength and ductility has been also experimentally measured.

In the above case scenario, "structure evolution" was carried out at elevated/high temperature by hybrid Monte-Carlo (MC) application(s). Then the evolved structure containing various types of SRCs were transferred to the "property prediction", where the compositional, thermodynamic and mechanical strengthening related properties were extracted.

Model Structure Input and Applied Methods

In the above case scenario, the simulation methods employed for evolution of local nano-structure of a high entropy alloy $Ta_{0.25}Nb_{0.25}Hf_{0.25}Zr_{0.25}$ and comparison of its evaluated Peierls stress/Critically Resolved Shear-Stress (CRSS) with its constituent metals are being discussed. The subsequent sections describe the initial structure related requirements, methodologies applied for local structure evolution and property predictions.

Structure Input:

To start this structure evolution and property prediction technique, alloy's average structure type, overall chemical composition, MD potentials (can be generated by this program/externally supplied) and heat treatment temperatures are required. Experimentally obtained lattice parameter (LP) of 3.43 Å was taken as the starting value for the alloy material. The initial LP may be taken from the rule of mixture of elemental lattice parameters or atomic volumes using Vegard's/Zen's law. The alloy system was created by creating a supercell of dimension 18×18×18 units oriented towards <1 0 0> type directions containing 11664 atoms. The atomic positions of this solid solution structure were assigned a statistically randomly distributed solid solution structure of the proper atomic composition by generating random numbers. Additionally, another structure was created which was oriented in X: [1 1 1], Y: [−1 1 0] and Z: [−1 −1 2] directions, which essentially is oriented along a slip direction [1 1 1] and edge dislocation slip plane (−1 1 0). This second structure had 48000 atoms. Both these structures were subjected to local structure evolution and then passed on to property prediction section. However, the initial structures may contain atoms in random order or in some predefined SRO/SRC order. The structure may also contain defects like line defects (edge, screw or mixed dislocations) or structural defects like vacancy loops or interstitial atoms.

For the molecular statics/dynamics simulations, an EAM type potential is required, which essentially consists of three parts: embedding function, pairwise interactions and electron densities around atoms. The potentials were created by taking inputs from accurate physical parameters for example, cohesive energy, unrelaxed vacancy formation energy, lattice parameters, atomic radius, second order elastic stiffness constants, anisotropic ratio, proper pairwise interaction formulas related to the elements Ta, Nb, Hf and Zr as mentioned in the above description.

Structure Evolution Method(s)

The structures that has been initialized, was passed on to the Monte Carlo application(s) with additional inputs from the heat treatment scheme(s). The TaNbHfZr alloy materials as initialized, was subjected to heat treatment annealing at 2000K temperature. For this, the LP of the initial average structure was adjusted. The alloy material containing 11664 atoms was subjected to NPT equilibration for 100 ps of simulation time and for a wide and discrete temperature range from 200-1500K. The obtained lattice parameters of the alloys were then fitted by regression and also quantitative/semi-quantitative estimate of coefficient of thermal expansion was obtained. The LP of the alloy to be annealed at 2000K was obtained from the data-fitted extrapolated linear curve.

The above structure was then recreated with the newly fitted LP for the temperature of interest. After this the scheme of Monte Carlo (MC) application(s) was employed. The above recreated structure was subjected to energy minimization using conjugate-gradient method and the potential energy of the system under consideration was recorded. Then, two random atoms were picked and their positions were interchanged (or swapped), and the system under consideration was subjected to minimization process. The potential energy was again recorded and then this swap of atom was accepted or rejected according to Metropolis type MC criterion based on the values of the potential energies. The LP was kept constant in all the energy minimization and MC swapping procedures. This process was repeated until the number of attempted atomic swaps was around 524880.

Property Prediction Method(s)

The evolved structures from the above described methods contain atomic coordinates and the element types. The local composition evolution of the simulated structures due to SRO/SRC/nano-precipitate formation can be calculated quantitatively/semi-quantitatively. This is done for the TaNbHfZr alloys by dividing the spatial co-ordinates in bins of width 3 Å as described above. Then the number of atoms of each element species in each bin were counted to get the atomic fraction and thus the local compositions.

Along with the MC steps running or getting executed, the internal potential energy of the system under consideration was also saved after every/specified interval of MC application(s) execution. The relative change of potential energy per atom was then calculated which provided a measure of the change in enthalpy ($\Delta H$) of the system under consideration. The change in configurational entropy ($\Delta S$) was calculated by scanning through the local compositions of the structure, or the number of bonds between different species with respect to (also referred as w.r.t and may be interchangeably used hereinafter) the atom's local neighbours.

The strengthening of the alloy under investigation can be determined by two major paths, one is "prediction without MD" and another by "prediction with MD" as described above by introducing additional defects and dislocations. In the case in scenario, both the ways have been briefly explored. Experimentally it was found that, with prolonged annealing of TaNbHfZr at 2073K, the hardness and Yield Strength (YS) had increased by 65% and 75%, respectively. The experiments for real validation purpose were carried out at the temperature at which it is very close to the temperature used in simulations (close to 3.5%). This can be explained by the change in local lattice potential energy/enthalpy due to the SRCs found by experimental characterizations, as well as by MC structure evolution simulations.

Other than the strengthening due to the long term annealing, at the initial formation stage of the alloy, strengthening of a factor around 4.9 was found w.r.t. the strength value obtained from the rule of mixture of the elemental constituents. This phenomenon of solid solution hardening was explained by introducing an edge dislocation in a commonly observed glide plane and stressing the dislocation to a shear slip direction. The stress required to move/glide the dislocation was simulated and noted for pure elements as well as for the random solid solution alloy and evolved structures containing SRCs. All these were done by a second set of MD simulations under the "properties prediction with MD" as described above.

Validation Outputs of the Simulated Results

In this section, the case under scenario, simulated results from this structure evolution and property prediction technique have been compared with experimentally obtained characterizations and measurements on the TaNbHfZr alloy system. The simulated results and their validations have been presented in accordance with example embodiment(s) as below:

Structure Evolution

MD Potential (MDP) File Creation/Generation:

The EAM type MD potential file generated/created for this alloy was based on accurate/proper elemental input parameters for example, but are not limited to, cohesive energy, unrelaxed vacancy formation energy, lattice parameters, atomic radius, second order elastic stiffness constants, proper pairwise interaction formulas. The following Table 1 shows the inputs that has gone in tabulating the EAM potential files (or MDP file) for the alloy.

TABLE 1

Physical input parameters for the created EAM potential (or MDP) file:

| Element | Atomic Radius (Å) | $E_c$ (eV) | $E_f$ (eV) | $C_{11}$ (eV/Å$^3$) | $C_{12}$ (eV/Å$^3$) | $C_{44}$ (eV/Å$^3$) |
|---|---|---|---|---|---|---|
| Tantalum (Ta) | 1.430 | 9.71 | 2.95 | 1.648 | 0.986 | 0.516 |
| Niobium (Nb) | 1.429 | 8.21 | 2.75 | 1.529 | 0.824 | 0.177 |
| Hafnium (Hf) | 1.572 | 7.56 | 2.39 | 0.818 | 0.643 | 0.281 |
| Zirconium (Zr) | 1.608 | 6.31 | 2.30 | 0.649 | 0.580 | 0.237 |

In the above Table 1, $E_c$ is cohesive energy, $E_f$ is unrelaxed vacancy formation energy, $C_{11}$, $C_{12}$ and $C_{44}$ are second order elastic constants for cubic systems.

Heat Treatment Scheme(s):

Temperature of the heat treatment/annealing was given as input (for user to select). The annealing temperature can be kept constant or varied from structure evolution sequence to sequence. Here the systems under consideration was evolved at 2000K. The annealing temperatures were kept constant and the MC structural evolution was carried out for until around 45 attempted atomic swaps have taken place.

Figure 3:
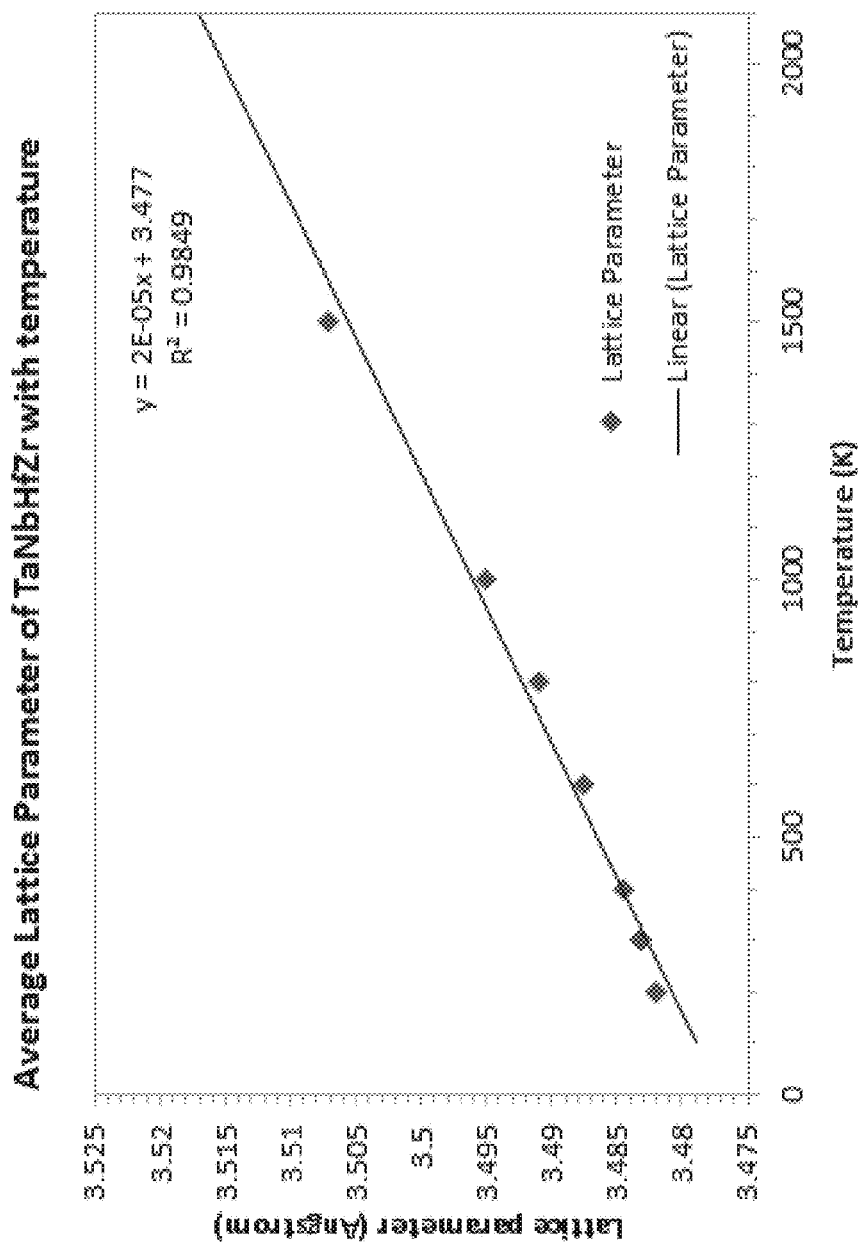
FIG. 3 depicts a graphical representation of a fitted straight line curve denoting Lattice Parameter (LP) of an alloy material (e.g., TaNbHfZr alloy material) for various temperatures in accordance with an embodiment of the present disclosure.

Initial Structure Equilibration:

The lattice parameter of the alloy composition under study was first determined in the initial structure equilibration technique. Average LP for the alloy for any given heat treatment temperature was obtained. FIG. 3, with reference to FIGS. 1 through 2, depicts a graphical representation of a fitted straight line curve denoting Lattice Parameter (LP) of the alloy material (e.g., TaNbHfZr alloy) for various temperatures in accordance with an embodiment of the present disclosure. The average structure LPs determined for annealing at 2000K was 3.52 Å.

Figure 4:
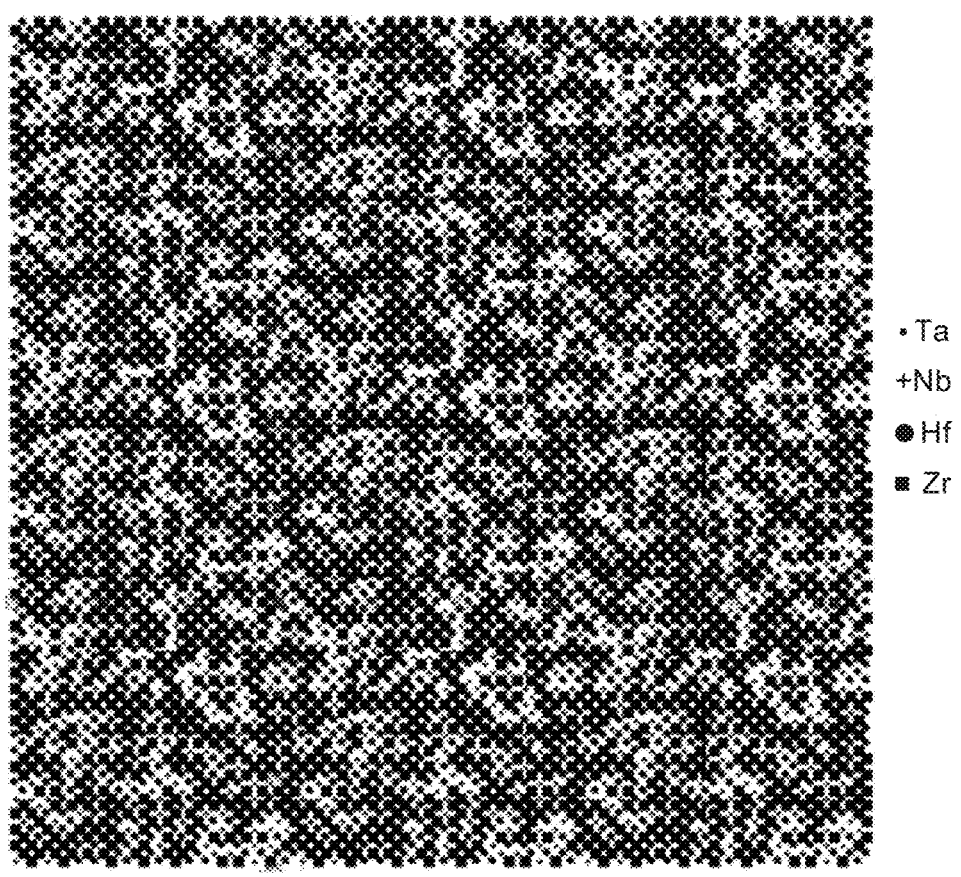
FIG. 4 depicts an initial spatial configuration containing atomic metallic elements of the alloy material with statistically random distribution of solid solutions in accordance with an embodiment of the present disclosure.

With the initial lattice parameter fixed, an alloy material supercell containing 11664 atoms of dimension ~6.3×6.3× 6.3 nm$^3$ was made (or created). FIG. 4, with reference to FIGS. 1 through 3, depicts an initial spatial configuration containing atomic metallic elements of the alloy material with statistically random distribution of solid solutions in accordance with an embodiment of the present disclosure. In FIG. 4, element Ta is represented by a small black dot (.), element Nb is represented by plus symbol (+), element Hf is represented by a slightly larger black dot (.), and element Zr is represented by a square solid block respectively.

Figure 5:
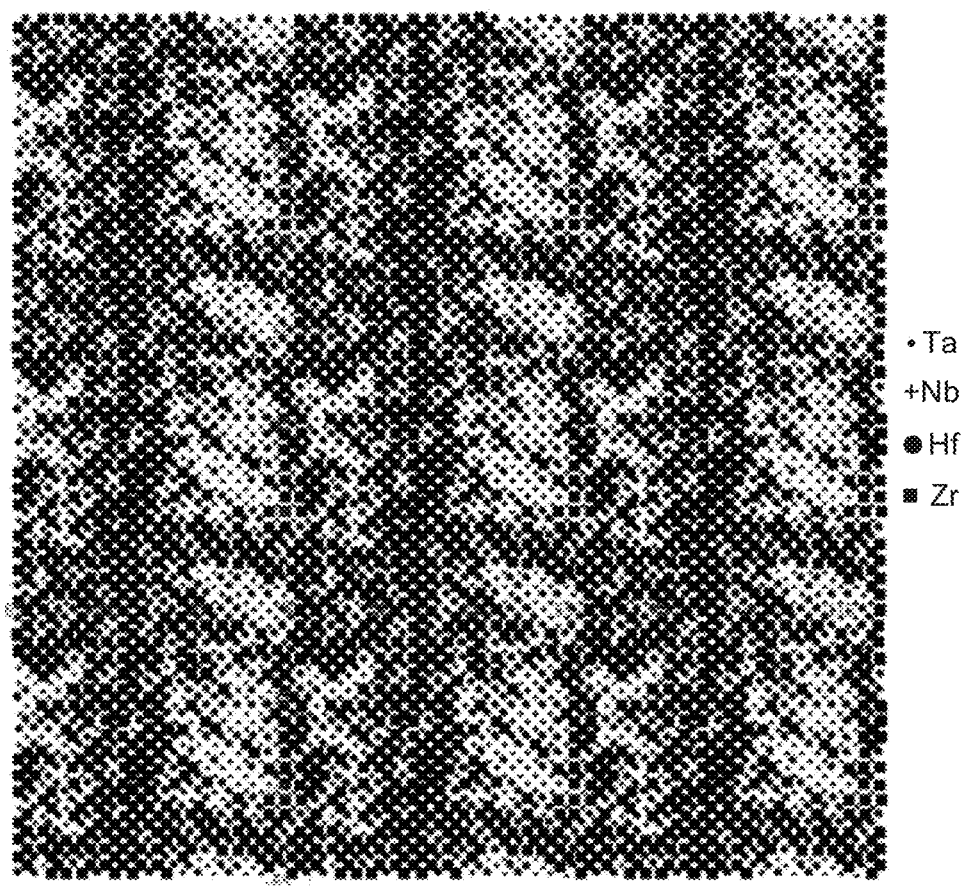
FIG. 5 depicts a local atomic structure of TaNbHfZr evolved at 2000K until 14 attempted MC swaps/atom in accordance with an example embodiment of the present disclosure.
Figure 6:
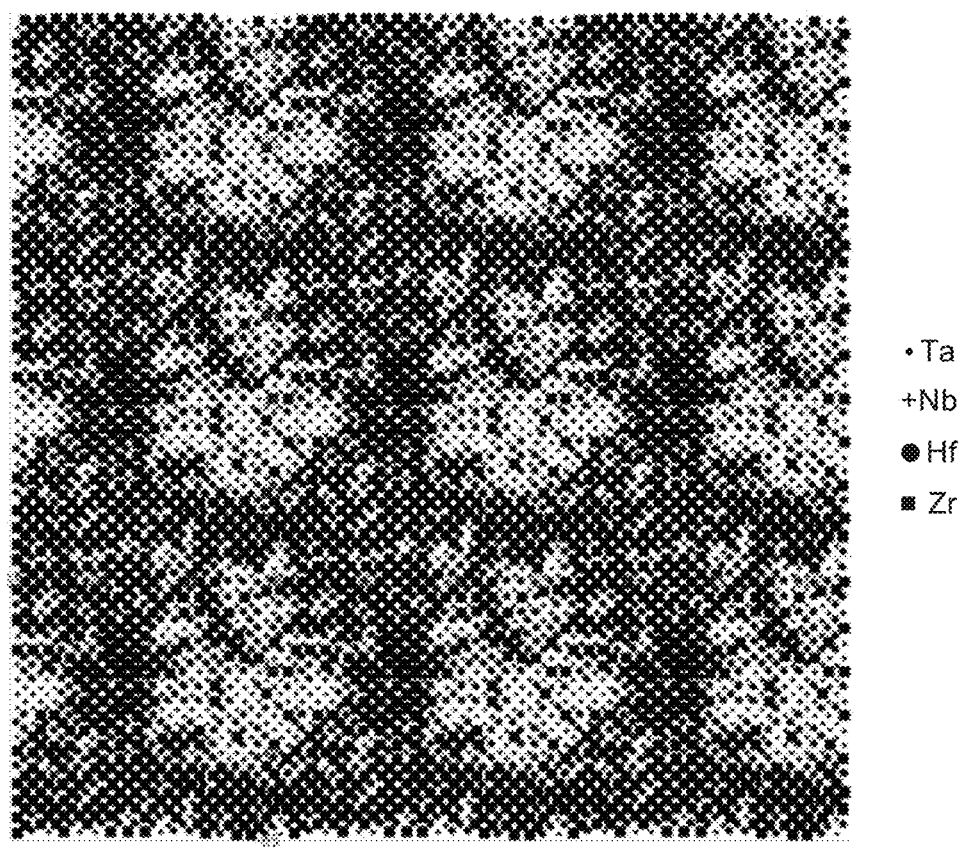
FIG. 6 depicts a local atomic structure of TaNbHfZr evolved at 2000K until 28 attempted MC swaps/atom in accordance with an example embodiment of the present disclosure.

Monte Carlo Application(s) Execution by the System 100:

Here the automatic structure evolution mode of MC simulation was chosen and after some MC atomic swaps the structures were presented as depicted in FIGS. 5 and 6. Here the MC simulation for structural evolution was carried out at 2000K. FIGS. 5 and 6 are placed sequentially so that it gives a visual impression of the evolution of the short-range clustering locally rich in mostly Zr and some Hf concentrations. More particularly, FIG. 5, with reference to FIGS. 1 through 4, depicts a local atomic structure of TaNbHfZr evolved at 2000K until 14 attempted MC swaps/atom in accordance with an example embodiment of the present disclosure. More particularly, FIG. 6, with reference to FIGS. 1 through 5, depicts a local atomic structure of TaNbHfZr evolved at 2000K until 28 attempted MC swaps/atom in accordance with an example embodiment of the present disclosure. Ta, Nb, Hf and Zr atoms (or atomic elements or chemical element) are plotted with different symbols as shown in FIGS. 5 and 6. In FIGS. 5 and 6, element Ta is represented by a small black dot (.), element Nb is represented by plus symbol (+), element Hf is represented by a slightly larger black dot (.), and element Zr is represented by a square solid block respectively. The structural evolution sequence is represented by number of attempted MC swaps per atom. In other words, FIGS. 5 and 6 show the local evolved and heat treated structures with 14 and 28 attempted MC swaps/atom. The atomic structure was graphically shown with its periodic neighbours so that the effect of SRC becomes visible with its compositional and directional effects. The plotting scheme of the different constituting elements with different symbols remain same as that of FIG. 4.

Structure Outputs:

While running the MC application(s) for structural evolution, the atomic coordinate files were saved at some intervals. These structure output files had 3D spatial coordinates of all atoms and their element types and atom identification number as a data file. Also the internal potential energy, MC swap probability and atomic identity numbers of swapping atoms were recorded throughout the whole MC application simulations or execution of the MC application(s).

Figure 7A:
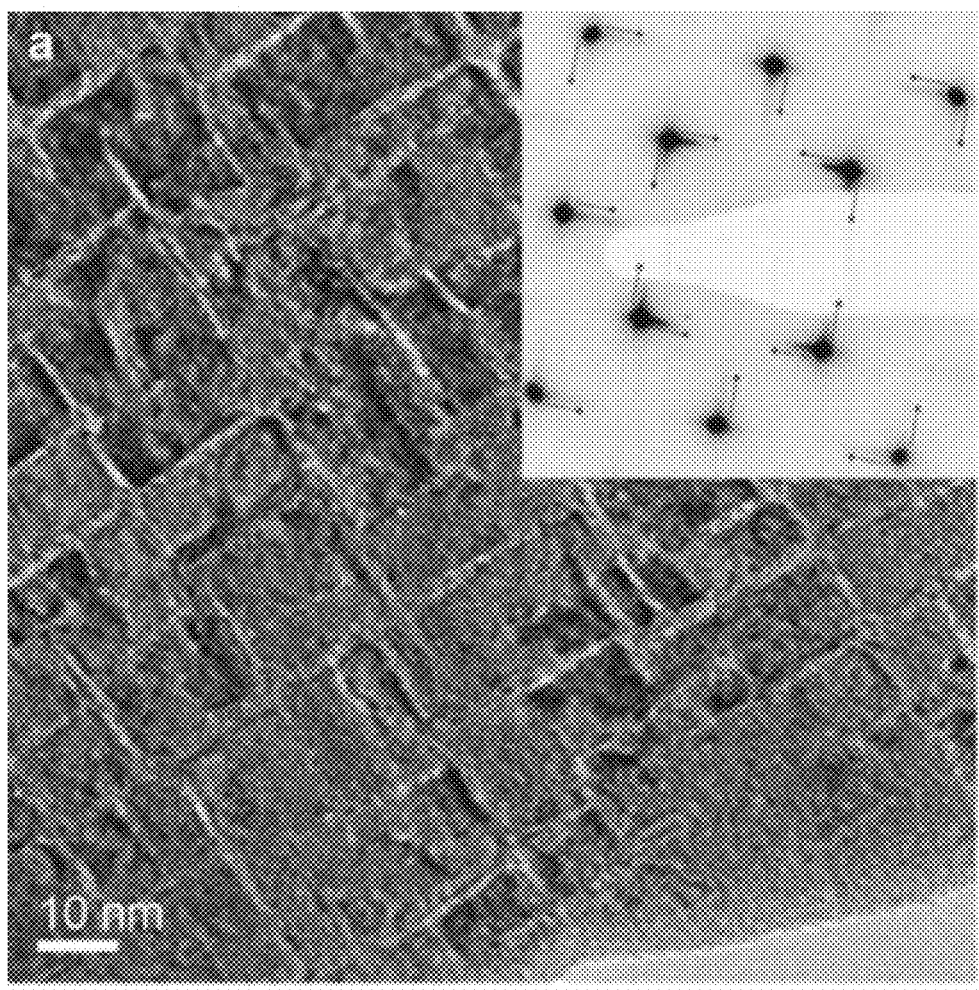
FIG. 7A depicts local structural domain-like features created by Short-Range Clusterings (SRCs) for the alloy annealed for 1 day in accordance with an example embodiment of the present disclosure.
Figure 7B:
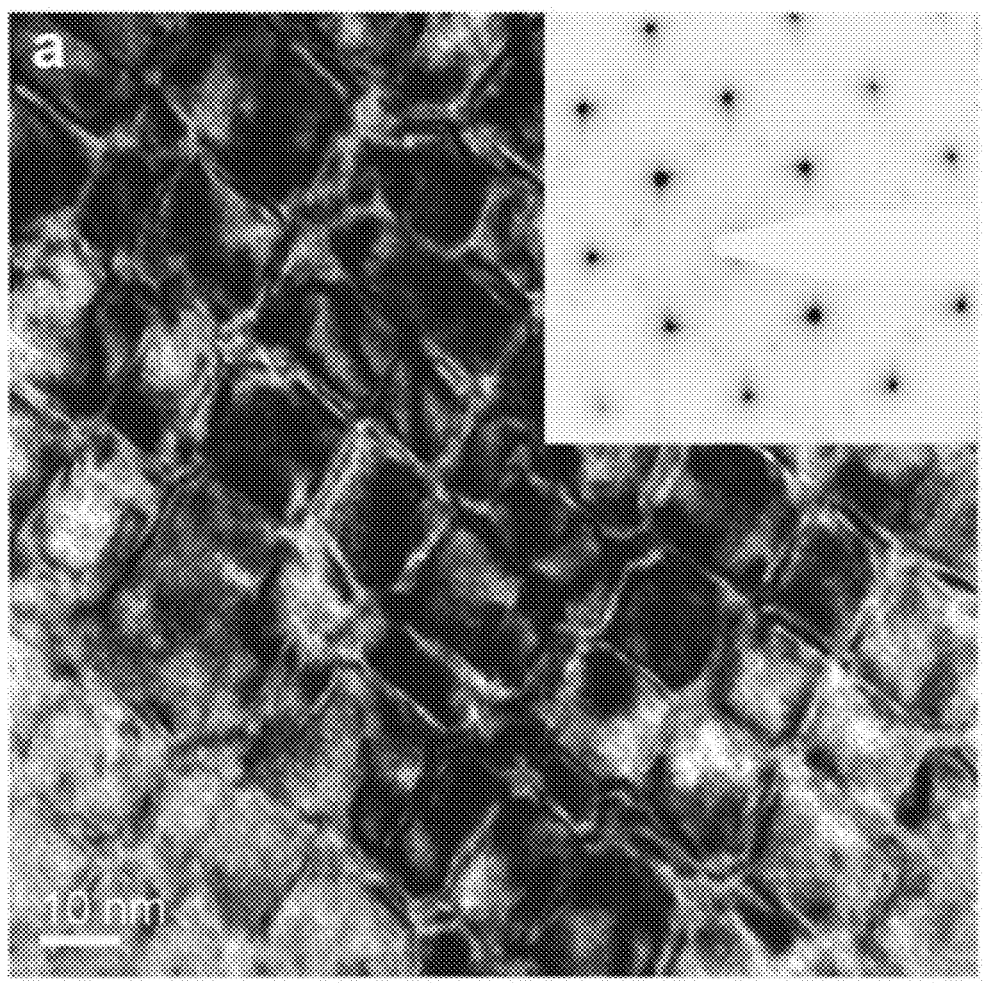
FIG. 7B depicts local structural domain-like features created by Short-Range Clusterings (SRCs) for the alloy annealed for 4 days in accordance with an example embodiment of the present disclosure.

Properties Prediction:

Atomic Positions Output:

The 3D atomic coordinate and individual atomic element types were saved as a data file and the atoms were first visualized in different data symbols. At a first glance in FIGS. 5 and 6, it can be found that Zr and Hf atoms have a tendency of clustering together, while Zr shows this tendency more. The whole simulated system slowly form interconnected directional SRCs appearing in the {1 0 0} set of crystallographic planes. Similar nano-structural features were also found in the high-resolution transmission electron micrograph on the heat treated TaNbHfZr alloys experimentally. FIG. 7A, with reference to FIGS. 1 through 6, depicts local structural domain-like features created by Short-Range Clusterings (SRCs) for the alloy annealed for 1 day in accordance with an example embodiment of the present disclosure. FIG. 7B, with reference to FIGS. 1 through 7A, depicts local structural domain-like features created by Short-Range Clusterings (SRCs) for the alloy annealed for 4 days in accordance with an example embodiment of the present disclosure. In the inset of the FIGS. 7A and 7B, the selected area electron diffraction (SAED) pattern (denoted by 702) is also included, which shows a main spot pattern of average body-centered cubic structure and also some diffuse streaks (shown with tiny alloys in 7A) which indicates the presence of directional SRO/SRCs.

The High-Resolution Transmission Electron Microscopy (HRTEM) images depicted in FIGS. 7A and 7B show remarkable resemblance with the simulated evolved structures by the MC application(s) executed and implemented by the system 100. The similarities between simulated and experimental nanostructures were found in terms of the directionality of the evolving SRCs, their gradual growth and interconnectivity. The above simulated and experimental FIGS. show that with longer annealing time, the SRCs grow and touch each other so that the alloy matrix gets divided into cuboid-like local domains.

Figure 8:
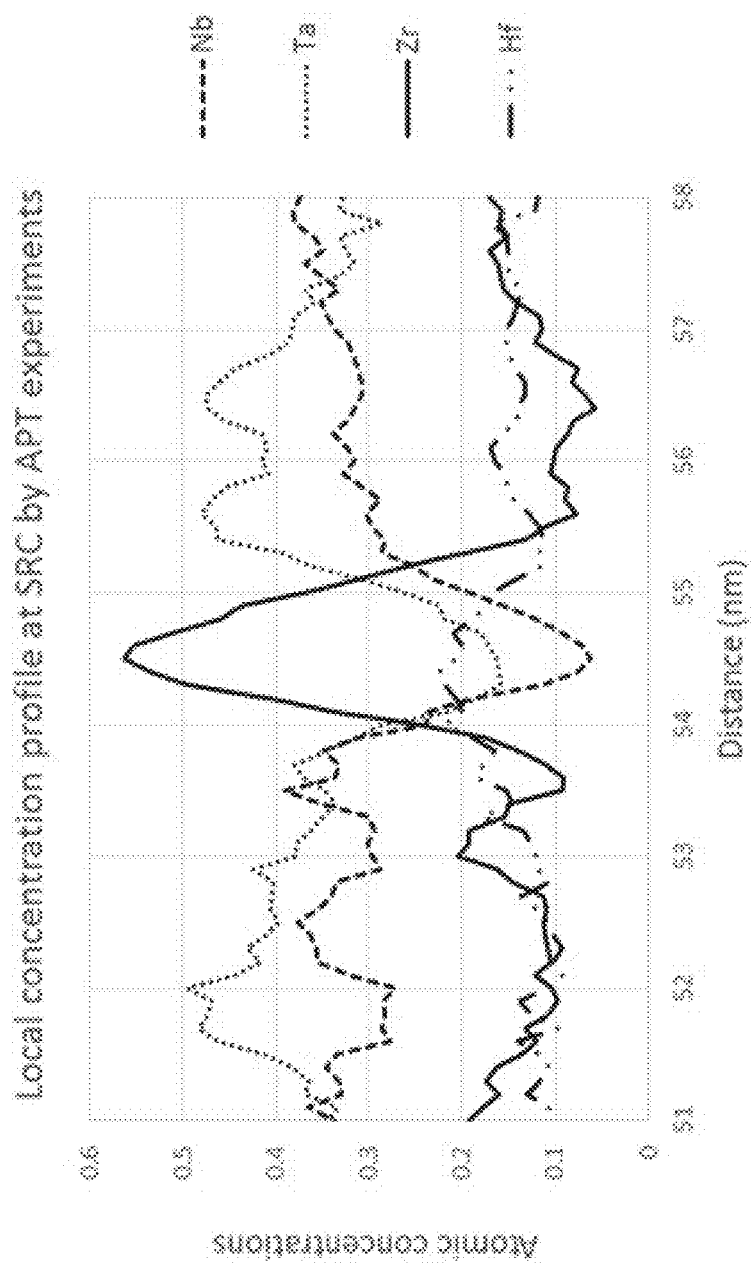
FIG. 8 depicts a graphical representation illustrating local atomic fractions across a planer SRC, experimentally obtained from Atom Probe Tomography (APT) reconstructions of annealed TaNbHfZr alloy material in accordance with an example embodiment of the present disclosure.
Figure 9:
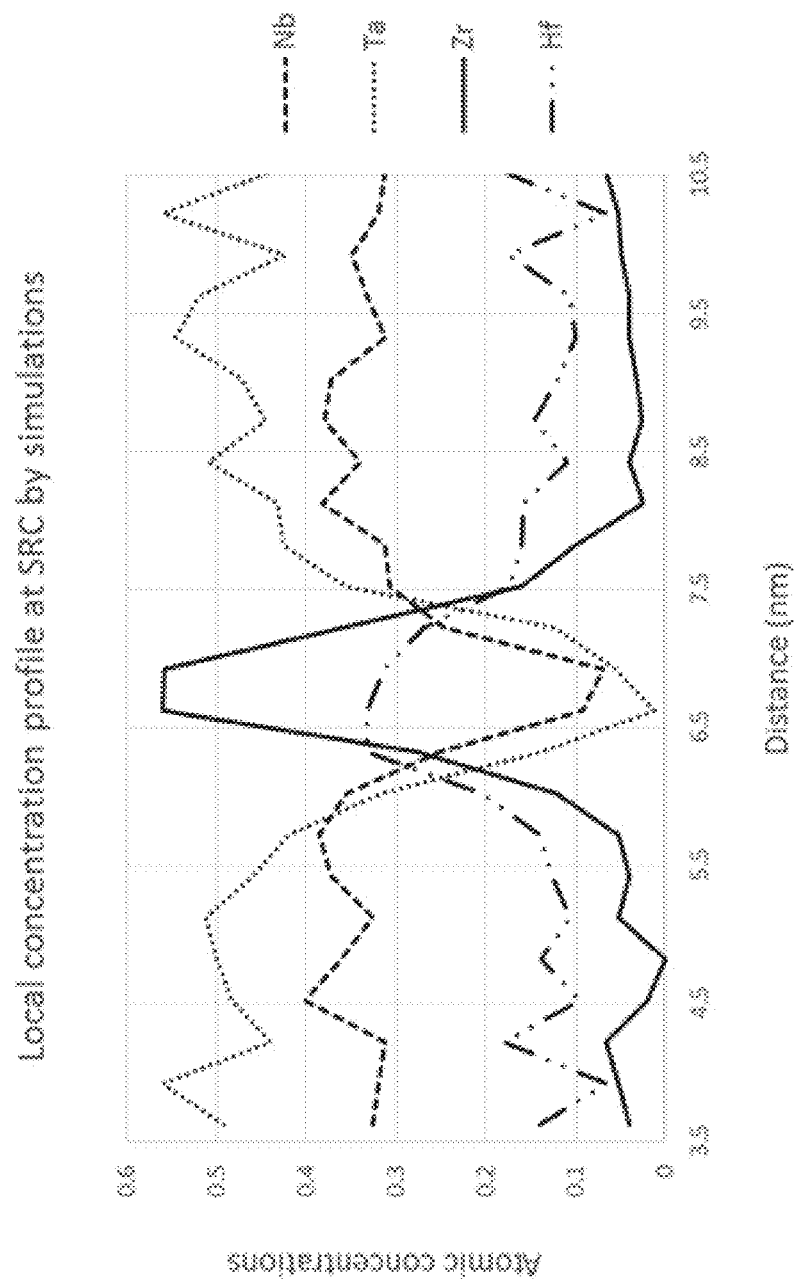
FIG. 9 depicts a graphical representation illustrating local atomic fractions across a planer Short-Range Clustering (SRC), obtained from Monte Carlo (MC) structure evolutions and binning analysis of annealed TaNbHfZr alloy material in accordance with an example embodiment of the present disclosure.

The local elemental composition across the SRCs in annealed TaNbHfZr alloy were measured experimentally from the compositional mapping by atom probe tomography (APT). The composition scan for atomic fraction is presented w.r.t the spatial distance as shown in FIG. 8. More specifically FIG. 8, with reference to FIGS. 1 through 7B, depicts a graphical representation illustrating local atomic fractions across a planer SRC, experimentally obtained from Atom Probe Tomography (APT) reconstructions of annealed TaNbHfZr alloy material in accordance with an example embodiment of the present disclosure. Similarly, local atomic fractions across SRC as obtained from the MC evolved structure w.r.t spatial distance, is plotted in FIG. 9. More specifically, FIG. 9, reference to FIGS. 1 through 8, depicts a graphical representation illustrating local atomic fractions across a planer Short-Range Clustering (SRC), obtained from Monte Carlo (MC) structure evolutions and binning analysis of annealed TaNbHfZr alloy material in accordance with an example embodiment of the present disclosure. The local compositions from the MC evolved structures were extracted by doing binning analysis as discussed in the above description.

It could be found from both experiment and simulations that the evolved SRCs are greatly rich in Zr concentration and depleted in Ta and Nb concentration, as compared to the surrounding alloy matrix. Also both experiment and simulations show similarity of certain degree of Hf co-clustering with Zr; and the full-width at half maximum (FWHM) of the SRCs w.r.t the local compositions in experiment and simulation are also comparable (around 10 Å).

Figure 10:
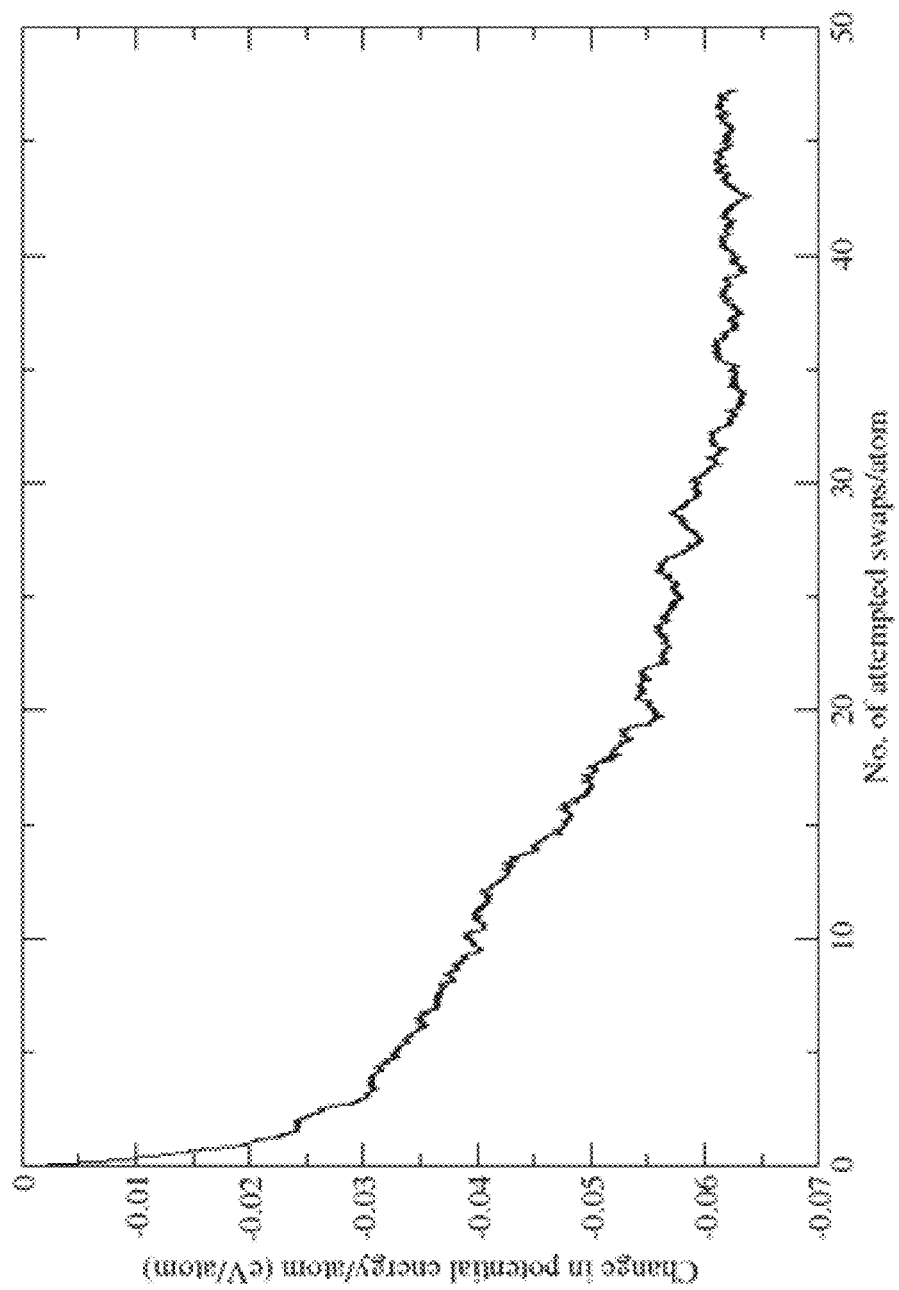
FIG. 10 depicts a graphical representation illustrating a change in thermodynamic enthalpy of MC evolved TaNbHfZr alloy material at 2000K in accordance with an example embodiment of the present disclosure.

Thermodynamic Output(s):

While evolving the structures by MC application(s) execution, the potential energies were noted after each MC atomic swaps. The relative change of the potential energy with respect to the very first configuration is here depicted as the change in thermodynamic enthalpy (ΔH, in units of electron volt/atom). FIG. 10 shows the change in ΔH of the simulated TaNbHfZr average alloy material evolved at 2000K w.r.t. the number of attempted MC swaps/atom. More specifically, FIG. 10, with reference to FIGS. 1 through 9, depicts a graphical representation illustrating a change in thermodynamic enthalpy of MC evolved TaNbHfZr alloy material at 2000K in accordance with an example embodiment of the present disclosure.

Prediction without Molecular Dynamics (MD):

In this type of properties prediction, the alloy material may not be subjected to any further MD simulations to predict further materials related properties.

Figure 11:
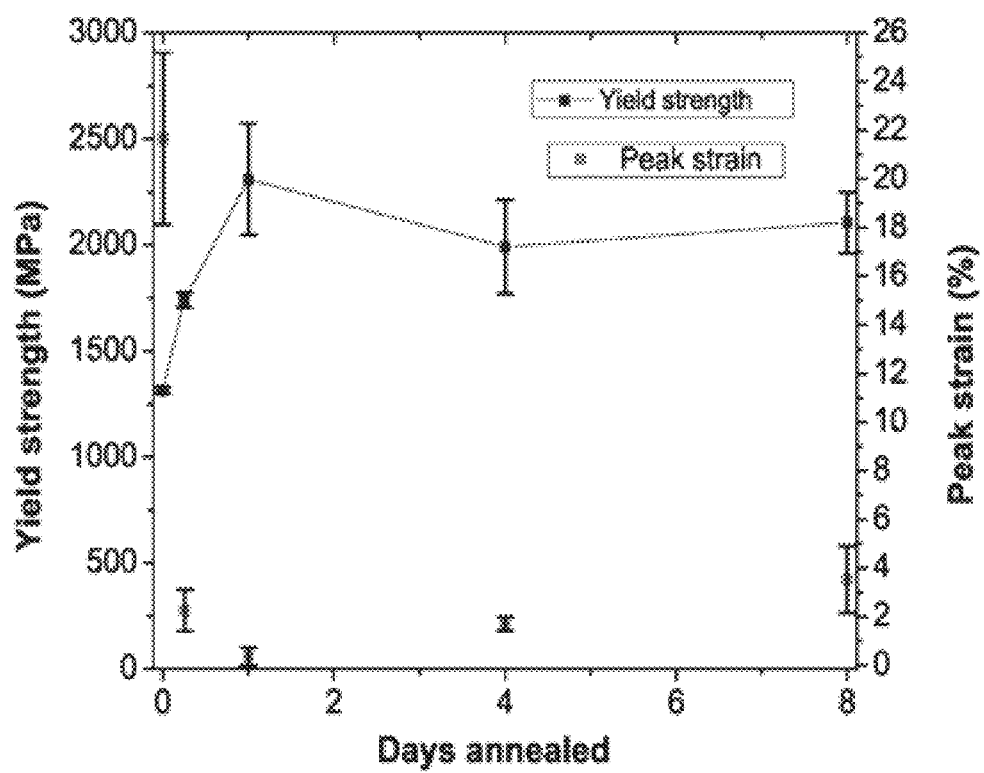
FIG. 11 depicts a graphical representation illustrating TaNbHfZr alloy material's compressive yield strength and ductility (peak strain to fracture) changes with annealing time in accordance with an example embodiment of the present disclosure.

Strengthening Due to SRO/SRC:

It has been found experimentally that upon annealing the TaNbHfZr alloy material, yield strength significantly went up as shown in FIG. 11. More specifically, FIG. 11, with reference to FIGS. 1 through 10, depicts a graphical representation illustrating TaNbHfZr alloy material's compressive yield strength and ductility (peak strain to fracture) changes with annealing time in accordance with an example embodiment of the present disclosure. Here the change in lattice energy by the formation of SRCs were calculated. If one planer SRC laying on the {1 0 0} type plane was introduced, the local change in lattice potential energy was calculated to be 62 meV/atom. This affects in creating local barriers for dislocation movements and hence extra strengthening effect of calculated 1079 MPa, which is close to the experimentally measured value of 995 MPa.

Prediction with MD:

In this type of properties prediction, additional MD techniques were applied on the MC evolved structures from the structure evolution section. Here in the case scenario, the effect of alloy strengthening in the TaNbHfZr alloy has been analysed as described below.

Figure 12:
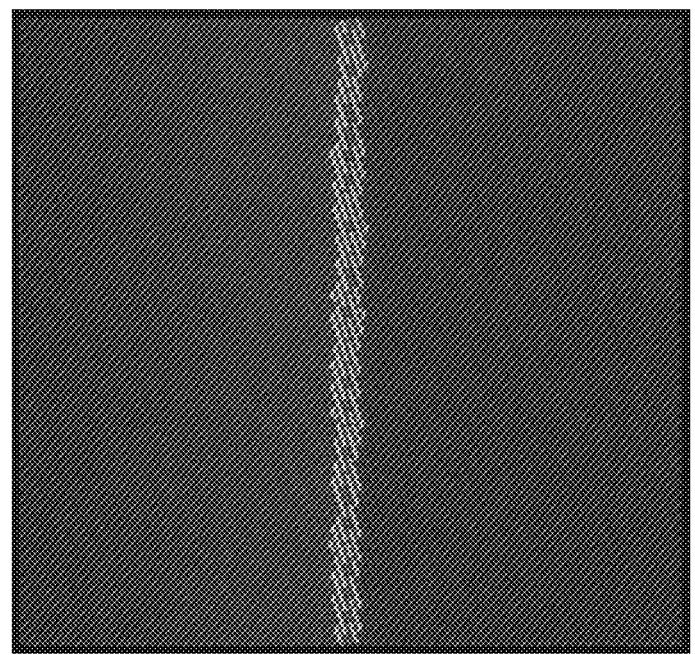
FIG. 12 depicts an edge-dislocation line introduced in a pure atomic metallic element (say pure Nb) in accordance with an embodiment of present disclosure.
Figure 13:
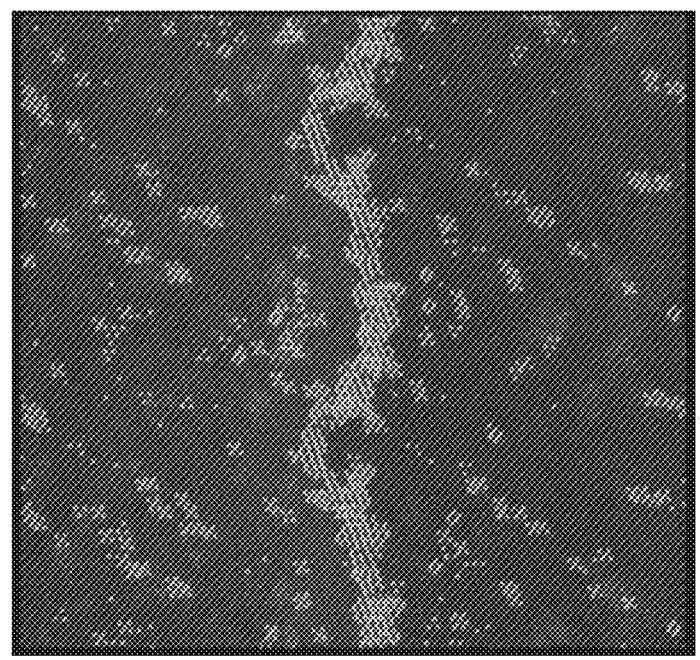
FIG. 13 depicts an edge-dislocation line introduced in MC evolved TaNbHfZr alloy material in accordance with an embodiment of present disclosure.

Addition of Dislocations:

In different MC evolved structures, edge type dislocations were introduced in a commonly occurring slip direction [1 1 1] and edge dislocation slip plane (−1 1 0) in BCC structures. The details of the dislocation creation is stated are discussed above in the description. However, before introducing dislocation, the alloy and pure element structures with around 48000 atoms were replicated with its periodic images so that volume of system under consideration (also referred as SUC and may be interchangeably used hereinafter) is increased by 2×2×2=8 times its original volume. This was done for pure elements of the alloy for example, Ta and Nb, initial alloy material and annealed alloys as well. The created dislocation line in Nb and annealed TaNbHfZr alloy material is shown in FIGS. 12 and 13, respectively. More specifically, FIG. 12, with reference to, FIGS. 1 through 11, depicts an edge-dislocation line introduced in a pure atomic metallic element (say pure Nb) in accordance with an embodiment of present disclosure. FIG. 13, with reference to, FIGS. 1 through 12, depicts an edge-dislocation line introduced in MC evolved TaNbHfZr alloy material in accordance with an embodiment of present disclosure. The continuous line of dislocation defect is visible with the white atoms, while the matrix atoms are grey atom dots, which retains the local BCC structural symmetry. The dislocation line in alloys appears to be locally kinky in nature, which suggests/indicates a locally distorted average lattice structure of the alloy.

Figure 14A:
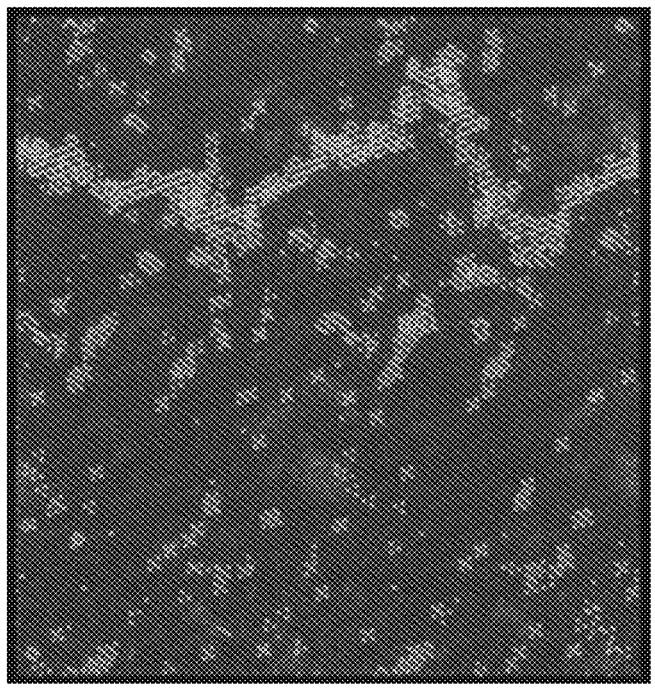
FIGS. 14A-14B show movement of dislocation line (from left to right) under application of shear stress in accordance with an example embodiment of the present disclosure.
Figure 14B:
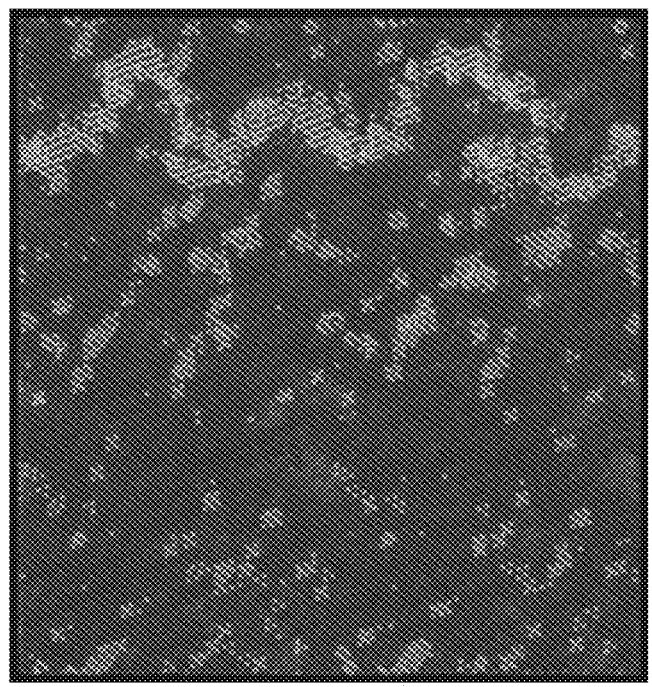

Deformation/Shear:

The introduced dislocation was created in the middle of the SUC and then shear force was applied on the top surface of the block of atoms, while keeping the bottom surface atoms fixed. This type of MD simulations were carried out at different shear-stress levels for systems with different degrees of structural evolution. FIGS. 14A-14B, with reference to, FIGS. 1 through 13, show movement of dislocation line (from left to right) under application of shear stress in accordance with an example embodiment of the present disclosure. More particularly, FIGS. 14A-14B show movement of edge dislocation (from left to right direction) in TaNbHfZr alloy material MC evolved for 5 attempted MC swaps/atom. The minimum shear stress required to move the dislocation called Critically Resolved Shear-Stress (CRSS) was noted for all systems under study (or SUC). The dislocation core remains kinky due to local lattice distortions. Additionally the dislocation line deviates from its initial linear nature to a rather zigzag nature due to its interaction with evolving SRCs.

Strengthening Properties:

The CRSS values of different pure elements and evolved alloy systems obtained at 50K is tabulated in Table 2. Table 2 gives a quantitative/semi quantitative measure of the alloy strengthening effect. Experimentally it was observed that the hardness and the compressive yield strength of the initial as synthesized condition of TaNbHfZr are 3575 MPa and 1315 MPa respectively, which are 2.4 and 4.9 times (strengthening factors), respectively, of what expected from the rule of mixture. After annealing treatment the yield strength touched a maximum of 2310 MPa. Similarly, from the CRSS values (Table 2) obtained from the property prediction with MD simulations, it is seen that there is a similar increasing trend in the values. The CRSS values of pure elements such as Ta and Nb have also been simulated for comparison with experimentally obtained values and calculation of the strengthening factors. The closeness of the simulation obtained CRSS values of Ta and Nb with the experimental values show the goodness of the developed EAM potential. It can be found that the CRSS of the initial TaNbHfZr alloy material is more than 2 times that of the pure elements. Also the CRSS values of the alloy go on increasing along with the number of MC swaps/atom. This corresponds to the additional strengthening effect of the alloy due to the formation of increasing amount of SRCs, which have been experimentally also found and depicted in FIG. 11.

TABLE 2

Simulated CRSS values of TaNbHfZr alloys and pure elements at 50 K:

| CRSS Values of Element/Alloy (Edge dislocation movement) | Stress (Mpa) |
|---|---|
| Niobium | 342.5 |
| Niobium (Experimental value) | 250 |
| Tantalum | 250 |
| Tantalum (Experimental value) | 275 |
| HfNbTaZr-Initial | 725 |
| HfNbTaZr-After 2 attempted MC swaps | 775 |
| HfNbTaZr-After 5 attempted MC swaps | 825 |

The written description describes the subject matter herein to enable any person skilled in the art to make and use the embodiments. The scope of the subject matter embodiments is defined by the claims and may include other modifications that occur to those skilled in the art. Such other modifications are intended to be within the scope of the claims if they have similar elements that do not differ from the literal language of the claims or if they include equivalent elements with insubstantial differences from the literal language of the claims.

It is to be understood that the scope of the protection is extended to such a program and in addition to a computer-readable means having a message therein; such computer-readable storage means contain program-code means for implementation of one or more steps of the method, when the program runs on a server or mobile device or any suitable programmable device. The hardware device can be any kind of device which can be programmed including e.g. any kind of computer like a server or a personal computer, or the like, or any combination thereof. The device may also include means which could be e.g. hardware means like e.g. an application-specific integrated circuit (ASIC), a field-programmable gate array (FPGA), or a combination of hardware and software means, e.g. an ASIC and an FPGA, or at least one microprocessor and at least one memory with software modules located therein. Thus, the means can include both hardware means and software means. The method embodiments described herein could be implemented in hardware and software. The device may also include software means. Alternatively, the embodiments may be implemented on different hardware devices, e.g. using a plurality of CPUs.

The embodiments herein can comprise hardware and software elements. The embodiments that are implemented in software include but are not limited to, firmware, resident software, microcode, etc. The functions performed by various modules described herein may be implemented in other modules or combinations of other modules. For the purposes of this description, a computer-usable or computer readable medium can be any apparatus that can comprise, store, communicate, propagate, or transport the program for use by or in connection with the instruction execution system, apparatus, or device.

The illustrated steps are set out to explain the exemplary embodiments shown, and it should be anticipated that ongoing technological development will change the manner in which particular functions are performed. These examples are presented herein for purposes of illustration, and not limitation. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope and spirit of the disclosed embodiments. Also, the words "comprising," "having," "containing," and "including," and other similar forms are intended to be equivalent in meaning and be open ended in that an item or items following any one of these words is not meant to be an exhaustive listing of such item or items, or meant to be limited to only the listed item or items. It must also be noted that as used herein and in the appended claims, the singular forms "a," "an," and "the" include plural references unless the context clearly dictates otherwise.

Furthermore, one or more computer-readable storage media may be utilized in implementing embodiments consistent with the present disclosure. A computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The term "computer-readable medium" should be understood to include tangible items and exclude carrier waves and transient signals, i.e., be non-transitory. Examples include random access memory (RAM), read-only memory (ROM), volatile memory, nonvolatile memory, hard drives, CD ROMs, DVDs, flash drives, disks, and any other known physical storage media.

It is intended that the disclosure and examples be considered as exemplary only, with a true scope and spirit of disclosed embodiments being indicated by the following claims.

What is claimed is:

1. A processor implemented method, comprising:
receiving, via one or more hardware processors, information pertaining to a plurality of atomic elements and a composition of each of the plurality of atomic elements, wherein
the composition of each of the plurality of atomic elements is specific to an alloy material, and
the plurality of atomic elements comprises one or more atomic metallic elements and one or more non-metallic elements;
calculating an embedded function for each of the plurality of the atomic elements and one or more parameters of a pairwise interaction of the plurality of atomic elements, wherein
the one or more parameters of the pairwise interaction includes force distance curves, the force distance curves being derived using input from physical constants,
the input from the physical constants comprises cohesive energy, vacancy formation energy, lattice parameters, atomic radius, second order elastic stiffness constants, and an anisotropic ratio, and
the calculation of the embedded function is based on the input from the physical constants;
generating, via the one or more hardware processors, a Molecular Dynamics Potential (MDP) file comprising sequential data of similar atomic interactions and dissimilar atomic interactions of the plurality of atomic elements, wherein the generation of the MDP file is based on the received information and the calculated embedded function;
generating, via a structure equilibration executed by the one or more hardware processors, a Three-Dimensional (3D) structure file for the composition of each of the plurality of atomic elements, by using the MDP file, wherein the 3D structure file comprises 3D coordinates for each of the plurality of atomic elements;
generating, via one or more Monte Carlo applications executed by the one or more hardware processors, an optimized evolved 3D structure file by using the 3D structure file and one or more heat treatment schemes, wherein
the optimized evolved 3D structure file comprises an atomic positions output and a thermodynamic output, and
a heat treatment schedule of the one or more heat treatment schemes is fed as an input to the one or more Monte Carlo applications,
one or more properties pertaining to the plurality of atomic elements and the composition are predicted by using the atomic positions output and the thermodynamic output,
the atomic positions output is generated by extracting atomic coordinates and atom types of output of the one or more Monte Carlo applications, and
the thermodynamic output comprises a lattice potential energy of the plurality of atomic elements, a change in entropy of the plurality of atomic elements, and local thermodynamic changes of the plurality of atomic elements, and
the one or more Monte Carlo applications are executed in an automatic operation mode;
stabilizing, during the automatic operation mode, an initial local structure of each of the plurality of atomic elements using temperature inputs from the one or more heat treatment schemes;

adding, based on absence of one or more line-defects and dislocations, the one or more line defects and the dislocations in the optimized evolved 3D structure file; and
predicting structure evolution and mechanical properties of the alloy material, wherein the prediction is based on each of:
(i) the addition of the one or more line defects and the dislocations, wherein the one or more line defects includes one of edge dislocations, screw dislocations, mixed dislocations, or interstitial loops,
(ii) executing deformation stress applications, wherein the deformation stress application is executed in a shear mode on a top surface the plurality of atoms, keeping a bottom surface of the plurality of atoms fixed to a subject,
(iii) using strengthening outputs, wherein the strengthening outputs refers to a means ratio of a deformation stress of an investigated material and a predicted deformation stress by pure elements,
(iv) creation of a fracture surface, wherein the creation of the fracture surface refers to creating a notch by deleting specific atoms of the plurality of atoms at a particular crystallographic input direction,
(v) using Fracture related outputs, wherein the Fracture related outputs are obtained by applying the stress at the notch,
(vi) executing Indentation simulation, wherein the indentation simulations are executed by pressing a first block of atoms of the plurality of atomic elements on a second block of atoms of the plurality of atomic elements,
(vii) executing Scratch simulation, wherein the Scratch simulation is performed by dividing the plurality of atoms into two groups, namely a scratch-indenter and an investigated alloy, and
(viii) using wear properties, wherein the wear properties are obtained by analyzing a surface plastic deformation of the plurality of atoms.

2. The processor implemented method of claim 1, wherein the atomic positions output comprises local composition of the plurality of atomic elements, Short-range-order (SRO) of the plurality of atomic elements, lattice distortion of local atomic structure of the plurality of atomic elements, local strains of the local atomic structure of the plurality of atomic elements, one or more defects, nano-clusters of the plurality of atomic elements, one or more morphological changes comprising distribution of the plurality of atomic elements, one or more Phase Field (PF) parameters, one or more interfaces of phases or clusters in the plurality of atomic elements, an evolution sequence of the alloy material, and real time-scale prediction of structure evolution of the alloy material.

3. The processor implemented method of claim 1, wherein the thermodynamic output further comprises at least one of change in enthalpy of the plurality of atomic elements, a change in Gibbs free energy of the plurality of atomic elements Stacking Fault Energy (SFE) of the plurality of atomic elements, and phonons of the plurality of atomic elements.

4. A system, comprising:
a memory storing instructions;
one or more communication interfaces; and
one or more hardware processors coupled to the memory via the one or more communication interfaces, wherein the one or more hardware processors are configured by the instructions to:

receive information pertaining to a plurality of atomic elements and a composition of each of the plurality of atomic elements, wherein
  the composition of each of the plurality of atomic elements is specific to an alloy material,
  the plurality of atomic elements comprises one or more atomic metallic elements and one or more non-metallic elements;
calculate an embedded function for each of the plurality of the atomic elements and one or more parameters of a pairwise interaction of the plurality of atomic elements, wherein
  the one or more parameters of the pairwise interaction includes force distance curves, the force distance curves being derived using input from physical constants,
  the input from the physical constants comprises cohesive energy, vacancy formation energy, lattice parameters, atomic radius, second order elastic stiffness constants, and an anisotropic ratio, and
  the calculation of the embedded function is based on the input from the physical constants;
generate a Molecular Dynamics Potential (MDP) file comprising sequential data of similar atomic interactions and dissimilar atomic interactions of the plurality of atomic elements, wherein the generation of the MDP file is based on the received information and the calculated embedded function;
generate, via a structure equilibration executed by the one or more hardware processors, a Three-Dimensional (3D) structure file for the composition of each of the plurality of atomic elements by using the MDP file, wherein the 3D structure file comprises 3D coordinates for each of the plurality of atomic elements;
generate, via one or more Monte Carlo applications executed by the one or more hardware processors, an optimized evolved 3D structure file by using the 3D structure file and one or more heat treatment schemes, wherein
  the optimized evolved 3D structure file comprises an atomic positions output and a thermodynamic output,
  a heat treatment schedule of the one or more heat treatment schemes is fed as an input to the one or more Monte Carlo applications,
  one or more properties pertaining to the plurality of atomic elements and a the composition are predicted by using at least one of the atomic positions output and the thermodynamic output,
  the atomic positions output is generated by extracting atomic coordinates and atom types of output of the one or more Monte Carlo applications,
  the thermodynamic output comprises a lattice potential energy of the plurality of atomic elements, a change in entropy of the plurality of atomic elements, and local thermodynamic changes of the plurality of atomic elements
  the one or more Monte Carlo applications are executed in an automatic operation mode;
stabilize, during the automatic operation mode, an initial local structure of each of the plurality of atomic elements using temperature inputs from the one or more heat treatment schemes;
add, based on absence of one or more line-defects and dislocations, the one or more line defects and dislocations in the optimized evolved 3D structure file; and predict structure evolution and mechanical properties of the alloy material, wherein the prediction is based on each of:
  (i) the addition of the one or more line defects and the dislocations, wherein the one or more line defects includes one of edge dislocations, screw dislocations, mixed dislocations, or interstitial loops,
  (ii) executing deformation stress applications, wherein the deformation stress application is executed in a shear mode on a top surface the plurality of atomic elements, keeping a bottom surface of the plurality of atomic elements fixed to a subject,
  (iii) using strengthening outputs, wherein the strengthening outputs refers to a means ratio of a deformation stress of an investigated material and a predicted deformation stress by pure elements,
  (iv) creation of fracture surface, wherein the creation of the fracture surface refers to creating a notch by deleting specific atoms of the plurality of atomic elements at a particular crystallographic input direction,
  (v) using Fracture related outputs, wherein the Fracture related outputs are obtained by applying the stress at the notch,
  (vi) executing Indentation simulation, wherein the indentation simulations are executed by pressing a first block of atoms of the plurality of atomic elements on a second block of atoms of the plurality of atomic elements,
  (viii) executing Scratch simulation, wherein the Scratch simulation is performed by dividing the plurality of atomic elements into two groups, namely a scratch-indenter and an investigated alloy, and
  (viii) using wear properties, wherein the wear properties are obtained by analyzing a surface plastic deformation of the plurality of atomic elements.

5. The system of claim 4, wherein the atomic positions output comprises local composition of the plurality of atomic elements, Short-range-order (SRO) of the plurality of atomic elements, lattice distortion of local atomic structure of the plurality of atomic elements, local strains of the local atomic structure of the plurality of atomic elements, one or more defects, nano-clusters of the plurality of atomic elements, one or more morphological changes comprising distribution of the plurality of atomic elements, one or more Phase Field (PF) parameters, one or more interfaces of phases or clusters in the plurality of atomic elements, an evolution sequence of the alloy material, and real time-scale prediction of structure evolution of the alloy material.

6. The system of claim 4, wherein the thermodynamic output further comprises at least one of a change in enthalpy of the plurality of atomic elements, a change in Gibbs free energy of the plurality of atomic elements Stacking Fault Energy (SFE) of the plurality of atomic elements, and phonons of the plurality of atomic elements.

7. One or more non-transitory machine readable information storage mediums comprising one or more instructions which when executed by one or more hardware processors cause:
  receiving, via the one or more hardware processors, information pertaining to a plurality of atomic elements and associated a composition of each of the plurality of atomic elements, wherein
    the composition of each of the plurality of atomic elements is specific to an alloy material and one or more non-metallic elements, the plurality of atomic elements comprises one or more atomic metallic elements and one or more non-metallic elements;

calculating an embedded function for each of the plurality of the atomic elements and one or more parameters of a pairwise interaction of the plurality of atomic elements, wherein the one or more parameters of the pairwise interaction includes force distance curves, the force distance curves being derived using input from physical constants, the input from the physical constants comprises cohesive energy, vacancy formation energy, lattice parameters, atomic radius, second order elastic stiffness constants, and an anisotropic ratio, and the calculation of the embedded function is based on the input from the physical constants;

generating, via the one or more hardware processors, a Molecular Dynamics Potential (MDP) file comprising sequential data of similar atomic interactions and dissimilar atomic interactions of the plurality of atomic elements based on the received information, wherein;

generating, via a structure equilibration executed by the one or more hardware processors, a Three-Dimensional (3D) structure file for composition of each of the plurality of atomic elements, by using the MDP file, wherein the 3D structure file comprises 3D coordinates for each of the plurality of atomic elements;

generating, via one or more Monte Carlo applications executed by the one or more hardware processors, an optimized evolved 3D structure file by using the 3D structure file and one or more heat treatment schemes, wherein the optimized evolved 3D structure file comprises an atomic positions output and a thermodynamic output, and a heat treatment schedule of the one or more heat treatment schemes is fed as an input to the one or more Monte Carlo applications, one or more properties pertaining to the plurality of atomic elements the composition are predicted by using the atomic positions output and the thermodynamic output, the atomic positions output is generated by extracting the atomic coordinates and the atom types of output of the one or more Monte Carlo applications, and the thermodynamic output comprises a lattice potential energy of the plurality of atomic elements, a change in entropy of the plurality of atomic elements, and local thermodynamic changes of the plurality of atomic elements, and the one or more Monte Carlo applications are executed in an automatic operation mode;

stabilizing, during the automatic operation mode, an initial local structure of each of the plurality of atomic elements using temperature inputs from the one or more heat treatment schemes;

adding, based on absence of one or more line-defects and dislocations, the one or more line defects and the dislocations in the optimized evolved 3D structure file; and predicting structure evolution and mechanical properties of the alloy material, wherein the prediction is based on each of:

(i) the addition of the one or more line defects and the dislocations, wherein the one or more line defects includes one of edge dislocations, screw dislocations, mixed dislocations, or interstitial loops, (ii) executing deformation stress applications, wherein the deformation stress application is executed in a shear mode on a top surface the plurality of atoms, keeping a bottom surface of the plurality of atoms fixed to a subject, (iii) using strengthening outputs, wherein the strengthening outputs refers to a means ratio of a deformation stress of an investigated material and a predicted deformation stress by pure elements, (iv) creation of a fracture surface, wherein the creation of the fracture surface refers to creating a notch by deleting specific atoms of the plurality of atoms at a particular crystallographic input direction, (v) using Fracture related outputs, wherein the Fracture related outputs are obtained by applying the stress at the notch, (vi) executing Indentation simulation, wherein the indentation simulations are executed by pressing a first block of atoms of the plurality of atomic elements on a second block of atoms of the plurality of atomic elements, (vii) executing Scratch simulation, wherein the Scratch simulation is performed by dividing the plurality of atoms into two groups, namely a scratch-indenter and an investigated alloy, and (viii) using wear properties, wherein the wear properties are obtained by analyzing a surface plastic deformation of the plurality of atoms.

8. The one or more non-transitory machine readable information storage mediums of claim 7, wherein the atomic positions output comprises local composition of the plurality of atomic elements, Short-range-order (SRO) of the plurality of atomic elements, lattice distortion of local atomic structure of the plurality of atomic elements, local strains of the local atomic structure of the plurality of atomic elements, one or more defects, nano-clusters of the plurality of atomic elements, one or more morphological changes comprising distribution of the plurality of atomic elements, one or more Phase Field (PF) parameters, one or more interfaces of phases or clusters in the plurality of atomic elements, an evolution sequence of the alloy material, and real time-scale prediction of structure evolution of the alloy material.

9. The one or more non-transitory machine readable information storage mediums of claim 7, wherein the thermodynamic output further comprises at least one of a change in enthalpy of the plurality of atomic elements, a change in Gibbs free energy of the plurality of atomic elements Stacking Fault Energy (SFE) of the plurality of atomic elements, and phonons of the plurality of atomic elements.

* * * * *